United States Patent
Djugash

(10) Patent No.: US 9,355,368 B2
(45) Date of Patent: May 31, 2016

(54) COMPUTER-BASED METHOD AND SYSTEM FOR PROVIDING ACTIVE AND AUTOMATIC PERSONAL ASSISTANCE USING A ROBOTIC DEVICE/PLATFORM

(71) Applicant: Toyota Motor Engineering & Manufacturing North America, Inc., Erlanger, KY (US)

(72) Inventor: Joseph M. A. Djugash, San Jose, CA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 547 days.

(21) Appl. No.: 13/828,364

(22) Filed: Mar. 14, 2013

(65) Prior Publication Data

US 2014/0279733 A1 Sep. 18, 2014

(51) Int. Cl.
| | |
|---|---|
| *G06F 15/18* | (2006.01) |
| *B25J 9/00* | (2006.01) |
| *G06N 99/00* | (2010.01) |
| *B25J 19/02* | (2006.01) |
| *B25J 13/08* | (2006.01) |
| *B25J 11/00* | (2006.01) |
| *G06F 19/00* | (2011.01) |

(52) U.S. Cl.
CPC .................. *G06N 99/005* (2013.01); *B25J 9/00* (2013.01); *B25J 11/008* (2013.01); *B25J 13/08* (2013.01); *B25J 19/023* (2013.01); *B25J 19/026* (2013.01); *G06F 15/18* (2013.01); *G06F 19/3418* (2013.01); *G06F 19/3443* (2013.01)

(58) Field of Classification Search
USPC .......................................................... 706/12
See application file for complete search history.

(56) References Cited

U.S. PATENT DOCUMENTS

| | | | |
|---|---|---|---|
| 5,913,212 | A | 6/1999 | Sutcliffe et al. |
| 6,549,939 | B1 | 4/2003 | Ford et al. |
| 6,792,427 | B2 | 9/2004 | Jackson |
| 7,543,233 | B2 | 6/2009 | Reponen et al. |

(Continued)

FOREIGN PATENT DOCUMENTS

EP 1314102 6/2009

OTHER PUBLICATIONS

Leewongjaroen09 (www.yankodesign.com/2009/05/I 4/dear-diarv-i-love-mÝ-robot; May 14, 2009).*

(Continued)

*Primary Examiner* — Jeffrey A Gaffin
*Assistant Examiner* — Nathan Brown, Jr.
(74) *Attorney, Agent, or Firm* — Snell & Wilmer LLP

(57) ABSTRACT

A method and a system for providing personal assistance in daily activities. A method and a system for actively and automatically providing personal assistance, using a robotic device/platform, based on detected data regarding a user and the user's environment. The method and system may include a processor, at least one sensor, an output device, a communications unit, and a database. The database may further include a memory and cloud-based database and computing. The method and system may provide assistance in jogging the memory of the user, parental control of a child, hazard detection, and various other circumstances. The method and system may actively and automatically provide personal assistance regarding health, exercise, diet, or nutrition. The method and system may assist the user or a health professional in health diagnosis and treatment.

39 Claims, 13 Drawing Sheets

(56) References Cited

U.S. PATENT DOCUMENTS

| | | |
|---|---|---|
| 2005/0091684 A1 | 4/2005 | Kawabata et al. |
| 2005/0234310 A1 | 10/2005 | Alwan et al. |
| 2006/0148528 A1 | 7/2006 | Jung et al. |
| 2011/0099142 A1 | 4/2011 | Karjalainen et al. |

OTHER PUBLICATIONS

Perez; "Intelligent, Context-Aware Personal Assistant App "Friday" Makes Its Public Debut"; Jul. 20, 2012.

DeVaul; "The Memory Glasses Project"; Oct. 28, 2013.

Armstrong et al.; "Using Smartphones to Address the Needs of Persons with Alzheimer's Disease"; Ann. Telecommun.; 65:485-495; 2010.

Coronato; "Smart Enviomments for Alzheimer's Patients"; Awareness Magazine; 2 pages; 2012.

Hammerl et al.; "Towards a Semi-Automatic Personal Digital Diary"; PETRA 2012; 8 pages; 2012.

Inglis et al.; "Issues Surrounding the User-Centered Development of a new Interactive Memory Aid"; Univ Access Inf Soc; 2:226-234; 2003.

Kores; "How Emotional Should the iCat Robot be?"; 76 pages; 2008.

Lee et al.; "Capturing and Reviewing Context in Memory Aids"; CHI 2006, Apr. 22-27, 2006; 4 pages.

Sanchez-Pi et al.; "A Smart Solution for Elders in Ambient Assisted Living"; IWINAC 2009; pp. 95-103; 2009.

www.yankodesign.com/2009/05/14/dear-diary-i-love-my-robot; May 14, 2009.

Busari; "Life-Logging Camera Brings New Hope for Memory-Loss Patients"; 3 pages; Nov. 5, 2009.

Pirttikangas et al.; "Know Your Whereabouts"; 7 pages; Nov. 15, 2012.

European Application No. 14155158.0 Extended European Search Report dated Apr. 2, 1015, 7 pages.

\* cited by examiner

COMPUTER-BASED METHOD AND SYSTEM FOR PROVIDING ACTIVE AND AUTOMATIC PERSONAL ASSISTANCE USING A ROBOTIC DEVICE/PLATFORM

BACKGROUND

1. Field

The present disclosure relates generally to a computer-based method and system of providing personal assistance in daily activities and more particularly, pertains to a method and system of automatically and actively providing personal assistance, using a robotic device/platform, based on detected data regarding the user and the user's environment.

2. Description of the Related Art

Most of robotic devices/platforms have been manipulators or industrial robots, such as conveyor robots for the purpose of automated or unmanned production operations in factories. Recently, research and development has advanced on the structure and application of mobile robots. Thus, expectations on the practical use of such mobile robots have increased. Other than industrial uses, uses of recent robot apparatuses include living uses, i.e., "symbiosis" uses with human beings or "entertainment" uses. These robots, regardless of their function, are generally limited in ability by their passive response programming.

Computing power is ever advancing. Records of data may be made with more ease than was previously obtainable. Prior personal assistance and memory jogging methods/systems have heavily relied upon passively outputting data based on an input/request from the user or upon occurrence of a predetermined or scheduled event stored in a database. However, currently, a computer-based method or system is needed for actively and automatically providing personal assistance to the user (e.g., actively and automatically reminding the user of an event or actively and automatically encouraging the user to take a particular action based on conversational and situational cues). Thus, a method/system is needed for detecting and processing data regarding the user and the environment surrounding the user, and actively and automatically providing personal assistance, using a robotic platform/device, based on the detected and analyzed data.

SUMMARY

The present invention relates generally to a computer-based method of providing personal assistance in daily activities and more particularly pertains to a system and method of automatically and actively providing personal assistance, using a robotic device/platform, based on detected data regarding the user and the user's environment.

In one embodiment, the present invention may be, for example, a computer-based method including the steps of: detecting, using at least one sensor, a first data associated with at least one person within a proximity of at least one of the at least one sensor; detecting, using the at least one sensor, a second data associated with an object, a living being, an event, a place, an environment, or combinations thereof within a proximity of at least one of the at least one sensor; selectively storing, using a processor, a learned data in a database based on the first detected data, the second detected data, a pre-programmed algorithm stored in the database, or combinations thereof; passively outputting, using a communications unit or an output device coupled to or in communication with the processor, a first output data upon a request received by the processor or a predetermined or scheduled event stored in the database; and actively and automatically outputting, using the communications unit or the output device, a second output data based on the first detected data, the second detected data, the learned data, the pre-programmed algorithm, or combinations thereof.

In another embodiment, the present invention may be a computer-based system, including the steps of: detecting, using at least one sensor, a first detected data associated with a person or a user within a proximity of at least one of the at least one sensor; detecting, using the at least one sensor, a second detected data associated with an object, a living being, an event, a place, an environment, or combinations thereof within a proximity of at least one of the at least one sensor; changing, using a processor or a controller, a current position of the robotic device or platform or at least one of the at least one sensor to a new position to increase the quantity of or improve the quality of the first detected data or the second detected data; analyzing, using the processor, the first detected data and the second detected data based on the learned data corresponding to the person, the object, the living being, the event, the place, the environment, or combinations thereof; selectively storing, using the processor, the learned data in a database based on the first detected data, the second detected data, a pre-programmed algorithm stored in the database, or combinations thereof; passively outputting, using a communications unit coupled to or in communication with the processor, a first output data upon a request received by the processor or a predetermined or scheduled event stored in the database; and actively and automatically outputting, using the communications unit, a second output data based on the analyzed first detected data, the analyzed second detected data, the learned data, the pre-programmed algorithm, or combinations thereof.

BRIEF DESCRIPTION OF THE DRAWINGS

Other systems, methods, features, and advantages of the present invention will be or will become apparent to one with skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Figure 1:
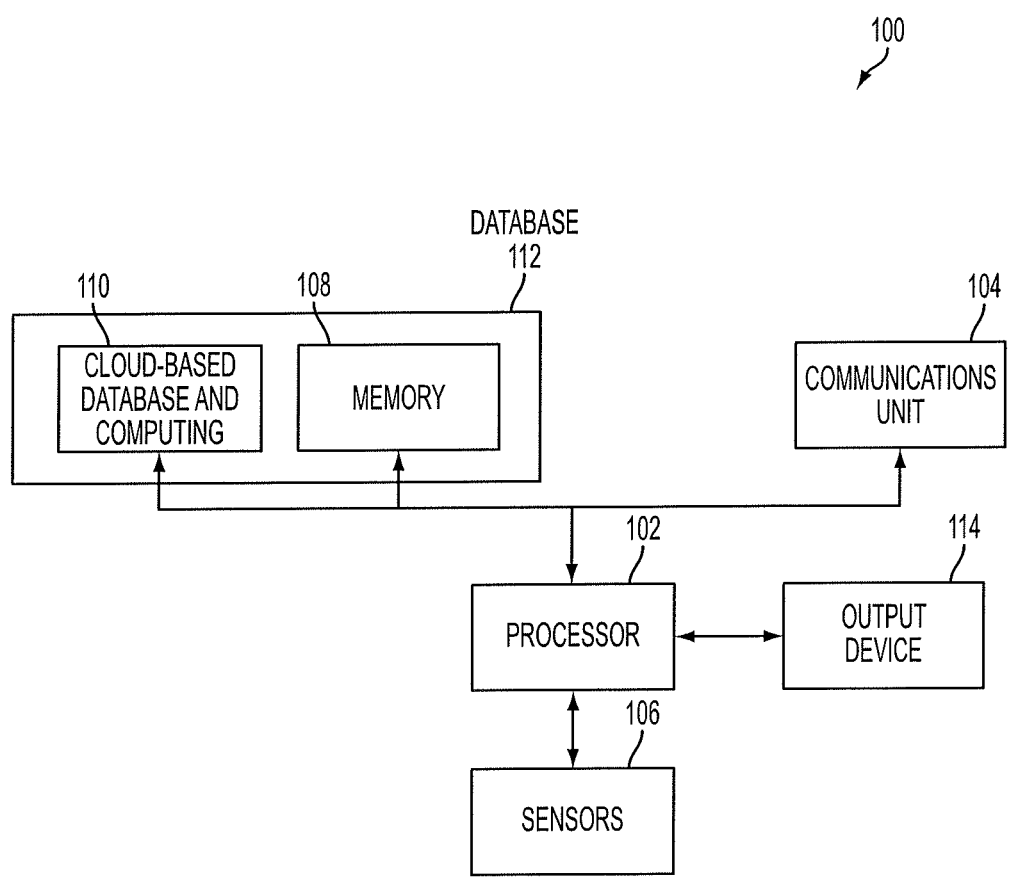
FIG. 1 is a block diagram of a computer-based system of automatically providing personal assistance using a robotic device/platform according to an embodiment of the present invention.

Referring to FIG. 1, a block diagram is shown of a method/system 100 according to an embodiment of the present invention. The method/system 100 may include a processor 102, a communications unit 104, sensors 106, a database 112, and an output device 114. The database 112 may include a memory 108 and cloud-based database and computing 110. In other embodiments, the database 112 may include solely the memory 108 or solely the cloud-based database and computing 110. The various units of the method/system 100 may be in communication with one another by utilizing transmission of an electronic signal through a Control Area Network (CAN) bus. In other embodiments, the control and communication may be over various other types of serial communication links, direct wirings, digital communication buses, wireless communications, or other communication links and networks.

In general, in the method/system 100, the database 112 stores a pre-programmed algorithm. The method/system 100 continuously detects a first detected data associated with a user or a person within a proximity of at least one of the sensors 106. The method/system 100 may further detect a second detected data associated with a static or dynamic object, a living being, a surrounding environment/place, and other detectable matters within the proximity of at least one of the sensors 106. In one embodiment, the method/system 100 not only outputs a first output data (using the communications unit 104 and/or using the output device 114) upon a request received by the processor 102 or a predetermined event stored in the database, but also actively and automatically outputs a second output data (via the communications unit 104 and/or using the output device 114). As such, the method/system 100 is configured to actively and automatically provide personal assistance to the user by detecting data regarding the user and the surrounding environment of the user, analyzing and cataloging the data, and outputting a second output data which can, for example, include helpful information as needed and as appropriate under the circumstances as determined by appropriateness algorithm rules described below (including but not limited to privacy concern rules). The processor 102 may modify or supplement the appropriateness algorithm rules based on the learned data. Analyzing and variants thereof, as used herein, may refer to, including but not limited to, any analysis, parsing, cataloging, or any other type of processing performed using detected data that may assist in storing data for later use, analyzing data to draw an inference, retrieving data, or outputting data.

The method/system 100 is not limited to any particular device, unit, or platform. In one embodiment, the method/system 100 is integrated in a robotic device or coupled to a robotic platform.

Referring to FIG. 1, in one embodiment, method/system 100 may utilize the sensors 106 to detect data within a proximity of the user, thereby allowing the processor 102 to draw inferences regarding the surrounding environment of the user. The processor 102 may then analyze the detected data in order to extract information and draw inferences that may enable the method/system 100 to assist the user in real time or store the analyzed data for automatically providing personal assistance at a later time. Such detected data may be related to persons, objects, events, places or any other information that the sensors 106 may detect in order to enable the processor 102 to draw inferences regarding any matter in an environment within a proximity of at least one of the sensors 106.

The sensors 106 may include converters that measure a physical quantity and convert the measured physical quantity into a signal which can be analyzed or processed by the processor 102. The sensors 106 may be any type of sensor and/or a plurality of sensors operating in concert together or independently. The sensors 106 may be integrated in or coupled to the method/system 100. The sensors 106 may be positioned at a distance away from the method/system 100 such that the sensors 106 are in communication with the processor 102, e.g., via a network. The processor 102 may be coupled to or in communication with one or more external devices in order to supplement the data detected by the sensors 106. The sensors 106 may be integrated in or coupled to an input/output communications interface, the output device 114, or various other devices or platforms without limiting the scope of the invention. For example, the input/output communications interface may be integrated in or coupled to a robotic device or platform.

The sensors 106 may detect a first detected data and/or a second detected data. The first detected data, as used herein, refers to any detected data that may assist the processor 102 in drawing an inference regarding a user or a person. The first detected data includes, but is not limited to, a physical appearance, motion, interaction, action, behavior, conversation, characteristic, location, identity, or combinations thereof of at least one person or a user within a proximity of the user or at least one of the plurality of sensors 106.

The second detected data, as used herein, refers to any data that may assist the processor 102 to draw an inference regarding any matter in an environment within a proximity of the user or at least one of the plurality of sensors 106. The second detected data includes, but is not limited to, a characteristic, location, condition, type or any attribute associated with an object, living being, surrounding place/environment within a proximity of at least one of the sensors 106, or any matters therein.

Proximity as used hereinafter refers to an area around the user or within the detection range of at least one of the sensors 106 within which data is sought to be collected. However, proximity, as used herein, is not limited to any particular distance range as the distance may vary depending on a detection range of the sensors 106, the extent of area in which data is sought to be collected, and various other design or practical factors or limitations. In another embodiment, the first detected data and/or the second detected data may not be limited to an environment within a proximity of the user. For example, in one embodiment, GPS data may be detected regarding a location that may be positioned well beyond the detection range of all of the sensors 106. The processor 102 may analyze the detected GPS data and automatically direct the communications unit 104 to output a second output data based on the detected GPS data.

In one embodiment, the sensors 106 may detect a robotic device/platform's environment or internal parameters of the robotic device/platform. In another embodiment, the sensors 106 may include sound and speech sensors such as a microphone capable of detecting speech, conversation, or sound. Speech as used herein may refer to speech, voice, or any other sound conveying information. In yet another embodiment, a three-dimensional (3-D) microphone may be utilized to detect speech and further pinpoint or detect the location of the source of the speech. The sensors 106 may further include an image sensor or a camera that may be integrated in, coupled to, or in communication with the method/system 100 for capturing images/videos. In one embodiment, when the user is indoors, a camera may be utilized as an external device placed in a stationary position that has a better vantage point for capturing and sensing data. The camera may be in communication with the processor 102, thereby transmitting the first detected data and/or the second detected data to the processor 102. For example, the camera may supplement the first detected data regarding the at least one person or user by capturing a visual facial feature of the user/person.

The sensors 106 may include positional encoders, compasses, navigational, and GPS sensors. The method/system 100 may be in communication with or coupled to a GPS system for supplementing the second detected data. For example, if the method/system 100 is mounted on a mobile unit (e.g., robotic device/platform), the sensors 106 may include an inertial measurement unit (IMU), which detects velocity, orientation, and gravitational forces of the mobile unit, using a combination of accelerometers, compasses, distance sensors, geomagnetic sensors, and gyroscopes. The sensors 106 may include various proximity/position sensors.

The sensors 106 may further include a capacitive displacement sensor, a passive thermal infrared sensor, a photocell (reflective) sensor, a radar sensor, a vibration sensor, a sonar sensor, and/or the like. The sensors 106 may also be configured to provide a user's current location and identify objects in the vicinity and/or within a geographic range. The sensors 106 may include perimeter monitoring sensors or ultraviolet, radio frequency, or infrared sensors. A 3-D scanner may be employed to analyze a real-world object or environment to collect data on its shape and its appearance (e.g., color). The detected data is then communicated to the processor 102 for constructing digital 3-D models.

The sensors 106 may further detect atmospheric pressure, smoke, and various other attributes of the environment within a proximity of the user. The sensors 106 may utilize thermistors to measure temperature. Based on the second detected data, the processor 102 may determine the type of the environment (e.g., a shopping mall, a parking lot, an office, and other place/environment characteristics). For example, the processor 102 may further determine a current temperature, a current moisture content, a current season or weather based on the second detected data. The sensors 106 may further include tactile sensors utilized to analyze contact with an object, person, living being, and others matters. In one embodiment, a touch sensor and/or a force sensor may be utilized to supplement the tactile information.

The sensors 106 may include sensors capable of detecting odor, magnetic fields, or radiation. Various other sensors may be integrated in, coupled to, or in communication with the sensors 106 in order to improve the quality or increase the quantity of the first detected data and/or the second detected data without limiting the scope of the invention.

If the method/system 100 is coupled to or incorporated within a mobile unit (e.g., a robotic device/platform, vehicle, transportation device, and the like), the mobile unit may traverse an environment within a proximity of the user. One advantage of traversing the environment is that the processor 102 may be in communication with the sensors 106 to improve the quality and/or increase the quantity of the first detected data and/or the second detected data. Furthermore, by traversing the environment within the proximity of the user, a 3-D visualization of the environment can be analyzed. For example, the robotic device/platform may traverse an environment or move closer to a person or object that has just entered the environment within a proximity of the user in order to place at least one of the sensors 106 in a better position to detect the first detected data and/or the second detected data. For example, the robotic device/platform may move intelligently to capture views of an occluded object, place, or a facial feature of a person. If the path has been previously traversed, the robotic device/platform may eliminate any backtracking that was previously performed.

Prior to a further detailed description of various embodiments of the method/system 100, an example of an application of the method/system 100 is provided.

Figure 2A:
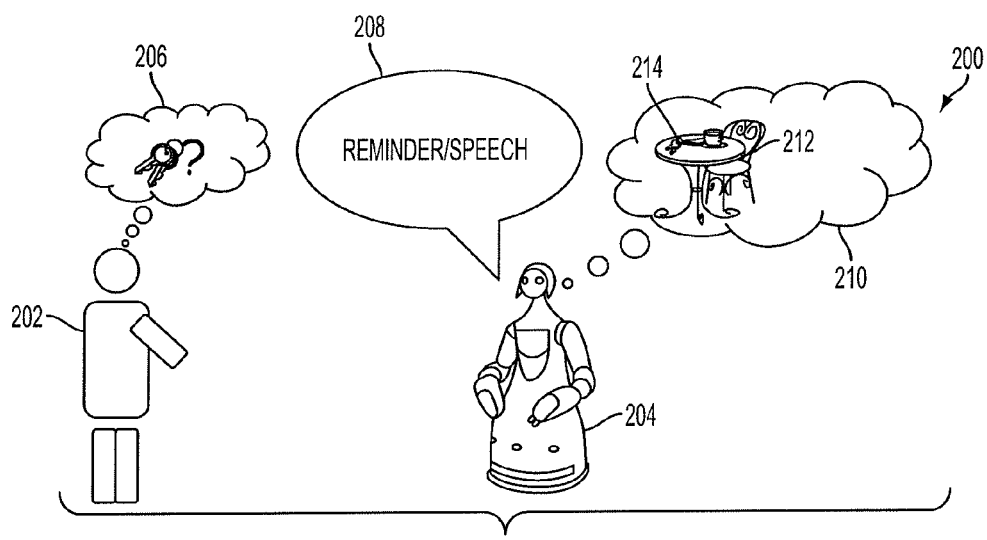
FIGS. 2A and 2B illustrate computer-based system implemented using a robotic device/platform configured to actively and automatically output data for providing personal assistance to a user and/or perform a mechanical operation according to an embodiment of the present invention.
Figure 2B:
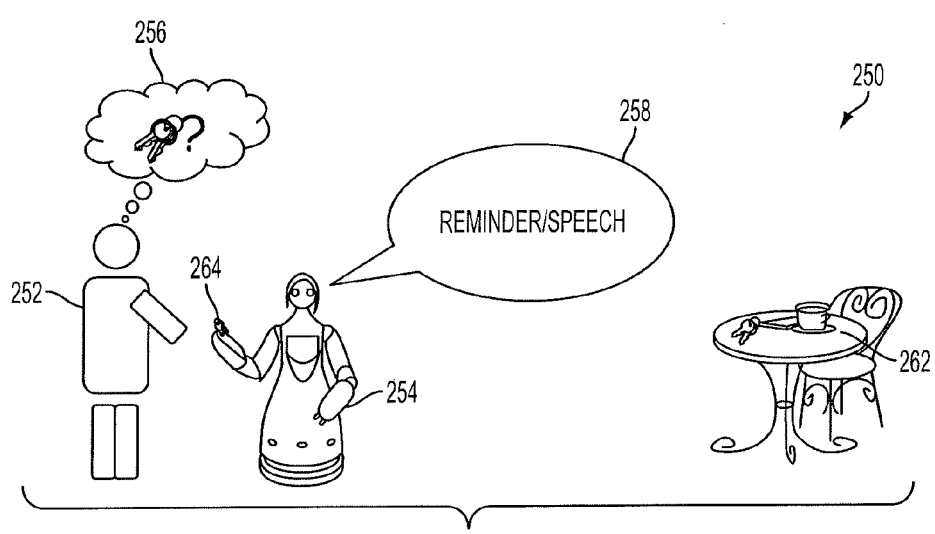

Referring to FIGS. 2A and 2B, the method/systems 200 and 250 serves as personal assistants in daily activities. The method/system 200 or 250 may be a software program implemented on a robotic device/platform 204 or 254, or on a computer coupled to or in communication with the robotic device/platform 204 or 254.

Referring to FIG. 2A, when the method/system 200 recognizes that the user 202 is searching for an object, i.e. key 214, the robotic device/platform 204 directs the user 202 to the key 214 by looking up prior relevant learned data and inferring context and interaction points. In an embodiment, the method/system 200 recognizes that the user 202 is searching for the key 214 and draws an inference 210 that the key 214 was placed on the table 212, by looking up prior relevant learned data. The method/system 200 directs the communications unit 104 or the output device 114 (e.g., a speaker) to output a second output data corresponding to relevant helpful information regarding the location of the key 214. The output device 114 may be integral to, coupled to, or in communication with the method/system 200.

Outputting relevant helpful information includes outputting a first output data upon an input/request from the user or upon occurrence of a predetermined/scheduled event, and actively and automatically outputting a second output data based on the first detected data and the second detected data and further based on a learned data. The learned data as used herein refers to currently or previously detected, processed, and stored data. The processor 102 may direct the robotic device/platform 204 to passively output a first output data when the processor 102 receives, using the sensors 106, or determines via the first detected data and/or the second detected data a request by the user 202 inquiring about the location of the key 214. The input/request may be received via: recognition of a facial expression detected by a camera and analyzed by the processor 102; an input/request received from the user 202 using a communication interface 218 (not shown) of the robotic device/platform 204; input/request from external devices coupled to or in communication with the robotic device/platform 204; other devices and methods of detecting an input/request; or combinations thereof.

However, an important aspect of the invention is that the method/system 200 is further configured to automatically output a second output data even without an input/request received from the user 202 and without occurrence of a predetermined or scheduled event. Recognition of the fact that the user 202 is searching for the key 214 can be performed using a combination of the sensors 106 described above. The method/system 200 is not limited to a particular sensor of the sensors 106 or any particular means of detecting such data.

In one embodiment, for example, if the user 202 utters a speech/thought 206, the sensors 106 detect the speech/thought 206. The processor 102 of the robotic device/platform 204 can analyze the speech/thought 206 by parsing the elements of the speech/thought 206 to determine that the user 202 is attempting to search for the key 214. Additionally or alternatively, a camera 216 (not shown) may be integrated in or coupled to the robotic device/platform 204. Alternatively or in addition, the robotic device/platform 204 may detect a facial expression of the user 202 indicating a sense of confusion as to the current location of the key 214. Other sensed data such as tactile data may be detected as well. By looking up prior relevant learned data about the key 214, the method/system 200 matches speech elements with the object (key 214) and actions, place, time, and the like associated with the object (key 214). The processor 102 of the method/system 200 directs the communication device 202 to output a second output data corresponding to relevant and appropriate information for assisting the user 202 in finding the key 214.

For example, the communication device 204 may generate an output reminder/speech 208 indicating to the user 202 that the key 214 is placed on the table 212. The communication device 204 may, alternatively or in addition, output a video recorded of the key 214 or the action of the user 202 placing the key 214 on the table 212. In one embodiment, the user 202 is only informed of the location of the object (key 214).

For example, using the sensors 106, a first detected data is continuously or intermittently detected regarding a user 202 or a person during daily activities. The sensors 106 further continuously or intermittently detect a second detected data regarding static or dynamic objects, living beings, place/environment, or combinations thereof within a proximity of the sensors 106. During daily activities of the user 202, the method/system 200 collect first data and/or second data associated with actions, interaction, speech, conversation, location, and other characteristics of the user 202 and the surrounding environment within a proximity of the user 202.

For example, the method/system 200 may have recognized, using the sensors 106 and the processor 102, that the key 214 was being placed on the table 212 based on a pre-programmed algorithm and previously detected, processed, and stored first data and/or second data as discussed in detail below. Given the first detected data and/or the second detected data regarding a person, the user 202, objects (e.g., the key 214 or the table 212), places (e.g., the home environment around the user 202), the speech/thought 206, other detected or stored data, or combinations thereof, the processor 102 of the method/system 200 can infer context and key interaction points or events. For example, a key interaction point in the embodiment shown in FIG. 2, may have been the event of "<person> placing <object1> on <object2>." The <person>, <object1>, and <object2> may correspond to the user 202, the key 214 and the table 212, respectively. The event of "<person> placing <object1> on <object2>" may be inferred from a sequence of detected events as follows: "<person> holding and/or touching <object1>," "<object1> touching and positioned above <object2>", "<person> at a distance from or not touching <object1>." Similarly, picking up an object may be recognized. For example, the event "<person> picking up <object1>" can be composed of a sequence such as "<object1> next to <person>," "<person> touches <object1>," and "<person> holding <object1>." As such, the method/system 200 may utilize algorithms of the like to automatically detect and analyze relatively high level events by recognizing a sequence of relatively lower level events. The algorithms may be adjusted or developed as the method/system 200 collects more first detected data and/or second detected data regarding the user 202 and the matters within the surrounding environment of the user 202.

The recognition of placement of the key 214 on the table 212 may have been via analyzing a conversation or speech indicating placement of the key 214 on the table 212. The recognition may alternatively or in addition be based on capturing image/video of the placement of the key 214. Upon using such a process for recognizing the various events within the surrounding environment of the user 202, the method/system 200 can create a journal summary of daily life of the user 202.

The method/system 200 may be applied in various applications and with respect to various objects and events to provide personal assistance to the user 202. For example, in an alternative embodiment, the method/system 200 may determine based on the combinations of data included in the first detected data and/or the second detected data whether the user 202 is thirsty or forgetful of where a bottle of water has been placed. The processor 102 of the robotic device/platform 204 can direct the communications unit 104 to output a second output data containing information as to the location of the water bottle.

As shown in FIG. 2B, in another embodiment, the robotic device/platform 254 may further transport the key 264 to the user 252. The robotic device/platform 254 may further have, for example, an arm that can be activated using actuators by use of pneumatic, hydraulic or electronic signals. The robotic arm may perform the gripping function to deliver the key 264 to the user 252 in addition to outputting the output reminder/speech 258.

Figure 3:
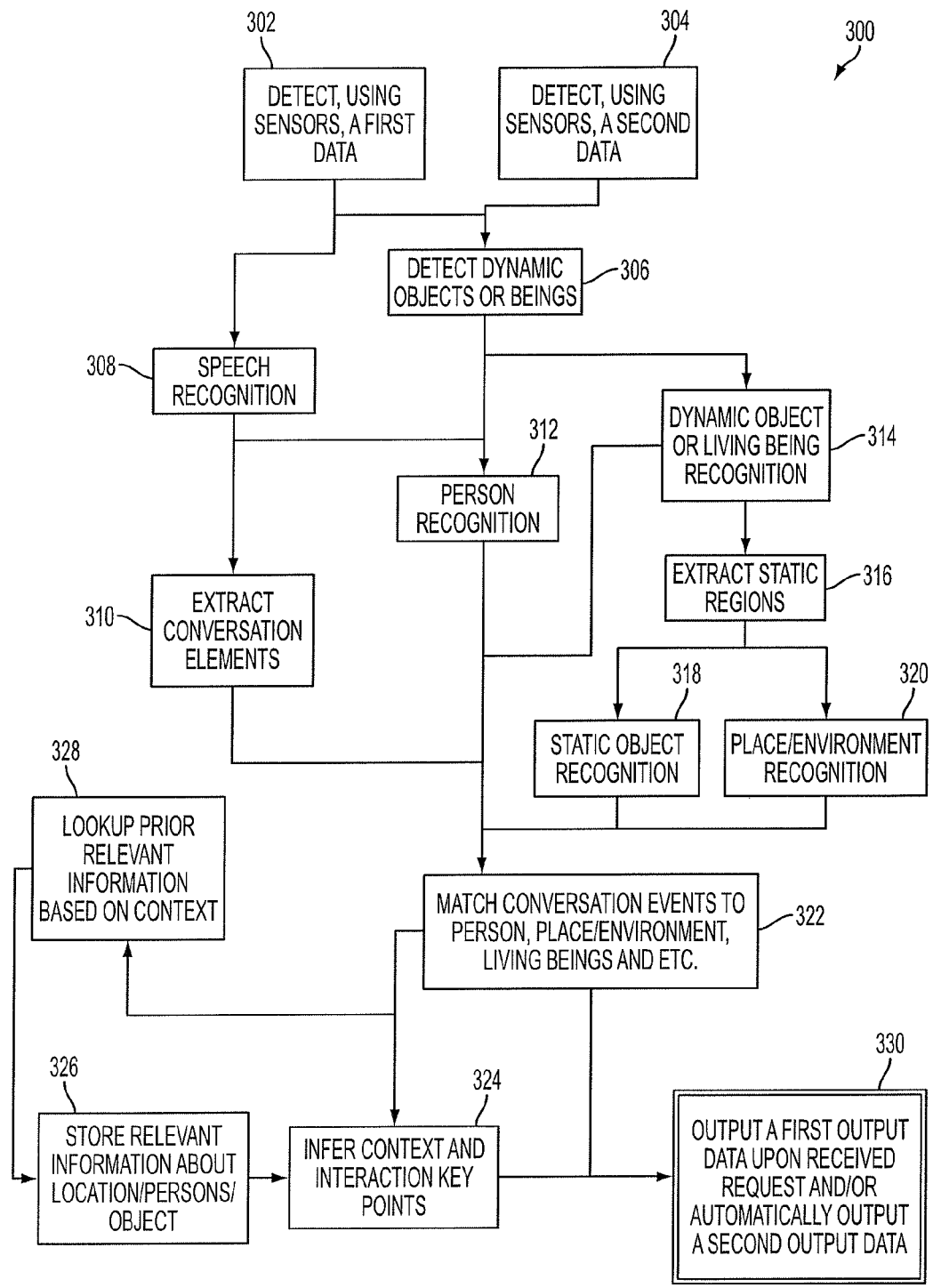
FIG. 3 is a decision flowchart diagram showing a computer-based method/system of outputting first and second output data based on the first detected data and the second detected data according to an embodiment of the present invention.

Referring to a flowchart of a method/system 300 shown in FIG. 3, in steps 302 and 304, the first data and the second data are detected using the sensors 106 as described above with respect to FIGS. 1 and 2. The method/system 300 is only an example of the detection and analysis or processing of the first detected data and/or the second detected data. The steps of method/system 300 may be performed simultaneously or in various combinations of orders. The degree to which data can be collected regarding the surrounding environment of the user and matters therein may depend on what or which sensors 106 are available and the processing limitations of the processor 102 and/or the cloud-based database and computing 110. As such, the method/system 300 may be adjusted accordingly in real time by monitoring such limitations.

The processor 102 may work in concert with the sensors 106 for improving collection of the first detected data and/or the second detected data. The processor 102 may also consider whether the user or a person is requesting or attempting to convey information. For example, if a user is making a facial expression without speech to communicate with the method/system 400, the processor 102 can direct the communications unit 104 to pose follow-up questions or inquiries using the communications unit 104 in order to supplement or clarify the detected data. For example, the method/system 300 may direct an output speech to be generated, thereby asking the user to clarify the facial expression. The user may then respond in a voice command clarifying the conveyed information.

In step 306, the method/system 300 detects dynamic objects or beings. In one embodiment, the method/system 300 may detect movement, changes in a scene or other dynamic regions as observed by cameras in order to focus the sensors 106 on the detected dynamic regions. The processor 102 classifies the detected dynamic region as described below.

For example, detection of a person, living being, and/or a dynamic object may be performed by looking for changes in data detected by the sensors 106. For example, changes in data detected by the camera may be determined. Changes in data received from the sensors 106 may be identified by first estimating the motion of the method/system 300 or a mobile platform upon which the method/system 300 is implemented, using GPS, IMU, or techniques such as visual odometry which allow estimation of the motion of a camera by tracking corner or blob features between two camera frames. As such, the method/system 300 may identify motion in the surrounding environment of the user which does not correspond to the motion of the method/system 300.

Upon identifying the changing parts of the scene within the first detected data and the second detected data, the method/system 300 seeks to recognize the changing elements, using techniques such as "eigenfaces" and "skeletal recognition" to recognize persons and faces. Additionally, standard techniques like Support Vector Machines, Deformable Parts Model and dynamic programming can be used to learn different models for various object/person classes. The types of features that can be used in these recognition tasks can be any combination of features like SIFT (Scale-Invariant Feature Transform), SURF (Speeded Up Robust Features), Gist modeling, Sobel, Fast, and other features and/or techniques that enable the method/system 300 to recognize a person, object, living being, or place/environment within a proximity of the user.

Thus, by detecting the dynamic regions, a new person entering the environment within the proximity of the user may be detected in step 312 and a dynamic object or being can be detected in step 306 and classified by the processor 102 in the database 112 accordingly. Simultaneously or thereafter, the method/system 300 extracts the remaining static regions in step 316. In one embodiment, in step 316 additional second detected data are collected form static objects in step 318 and from an environment or place within a proximity of the user in step 320.

The sensors 106 may utilize a microphone and a speech recognition module to detect speech, conversation or interaction as shown in step 308. The method/system 300 may further extract conversation elements containing useful data in step 310. In step 322, the processor 102 of the method/system 300 matches extracted conversation or speech elements from step 310 to the detected person, object, living being, place/environment, or combinations thereof.

In step 328, the method/system 300 looks up prior relevant information or learned data based on context and based on the matched conversation events from step 322 regarding the person, object, living being, place/environment, or combinations thereof. In step 326, the processor 102 stores relevant information for later use in the database 112 based on prior relevant information. For example, if the processor 102 detects facial features of a person entering the environment and also detects that the new person is speaking, the speech elements can be matched with the new person. Speech data related to the person may be stored in the database 112 for later use. A 3-D microphone or a microphone array may also be utilized to localize the origin of the sound or voice. The method/system 300 can track and log data related to the person in order to supplement the first detected data. The method/system 300 may actively and automatically output a second output data in step 330 based on the matched conversation events to the corresponding person, place/environment, living beings, or combinations thereof of step 322 and further based on the inferred context and interaction key points from step 324.

The processing of data (e.g., in steps 306-330) can be performed by continuously analyzing data gathered by the sensors 106 in real time. The cloud-based database and computing 110 may be utilized due to restraints on the information storage capacity of the memory 108 or energy capacity challenges associated with processing using solely the processor 102. However, in one embodiment, both on-board and off-board processing capabilities are utilized to prepare for events in which the on-board processing may be preferable (e.g., a poor connection in cloud communications) to ensure a minimal level of capability. For example, if the method/system 300 is implemented in a robotic device/platform that may not have sufficient capacity to perform the steps described herein, the cloud-based database and computing 110 can provide assistance in sharing the load of the processing.

In step 330, the processor 102 may passively output, using the communications unit 104, a first output data upon an input/request received by the processor 102 or a predetermined or scheduled event stored in the database 112.

The processor 102 may further actively and automatically output, using the communications unit 104, a second output data based on the first detected data and/or the second detected data, the previously detected, processed, and stored first and/or second data, the pre-programmed algorithm stored in the database 112, or combinations thereof.

As discussed above, the communications unit 104 allows the method/system 300 to communicate with the user or another person based on the detected data. The communications unit 104 may include a display screen or a projection system, integrated in the method/system 300 or in communication with the processor 102. For example, the first or second output data may be displayed via a display screen. The display screen may be desirable if the method/system 300 is implemented for a device requiring a compact design, such as a wheel chair. In one embodiment, the method/system 300 may utilize a display screen of a robotic device or platform for outputting the first and/or second output data.

In another embodiment, due to practical concerns, a projector in lieu of a display screen may be implemented in a robotic device/platform to project output images/videos on a wall, screen, or surfaces of the like based on the first and/or second output data. A projector may be preferable if the method/system 300 is designed for a robotic device/platform with characteristics requiring a compact design. The display may be, for example, a (color) liquid crystal display on which the second output data is displayed. The output images/videos may be displayed using an LCD, an organic light emitting display, a plasma display, light-emitting diodes, or any other display mechanism for displaying the output images/videos. The communications unit 104 may further include an audio output unit such as a speaker to communicate information to a user or a person. For example, the processor 102 may remind a user to recommend a course of action to the user via the speaker.

The processor 102 may further submit the first output data and/or the second output data to the output device 114 (e.g., another electronic device authorized by the user). In another embodiment, the output device 114 is coupled to or in communication with a device capable of performing mechanical movements. The processor 102 may output a third output data designed to direct a controller of the output device 114 to activate, operate, or control a movement of a mechanical device coupled to or integrated within the output device 114. For example, referring to FIG. 2, the mechanical movement may include moving towards the table 212, gripping the key 214 and bringing the key 214 to the user 202. The processor 102 may further be coupled to or in communication with the output device 114 integrated in or external to the method/system 300. The output device 114 may be any device capable of performing an operation or processing based on a third output data generated by the processor 102.

Figure 4:
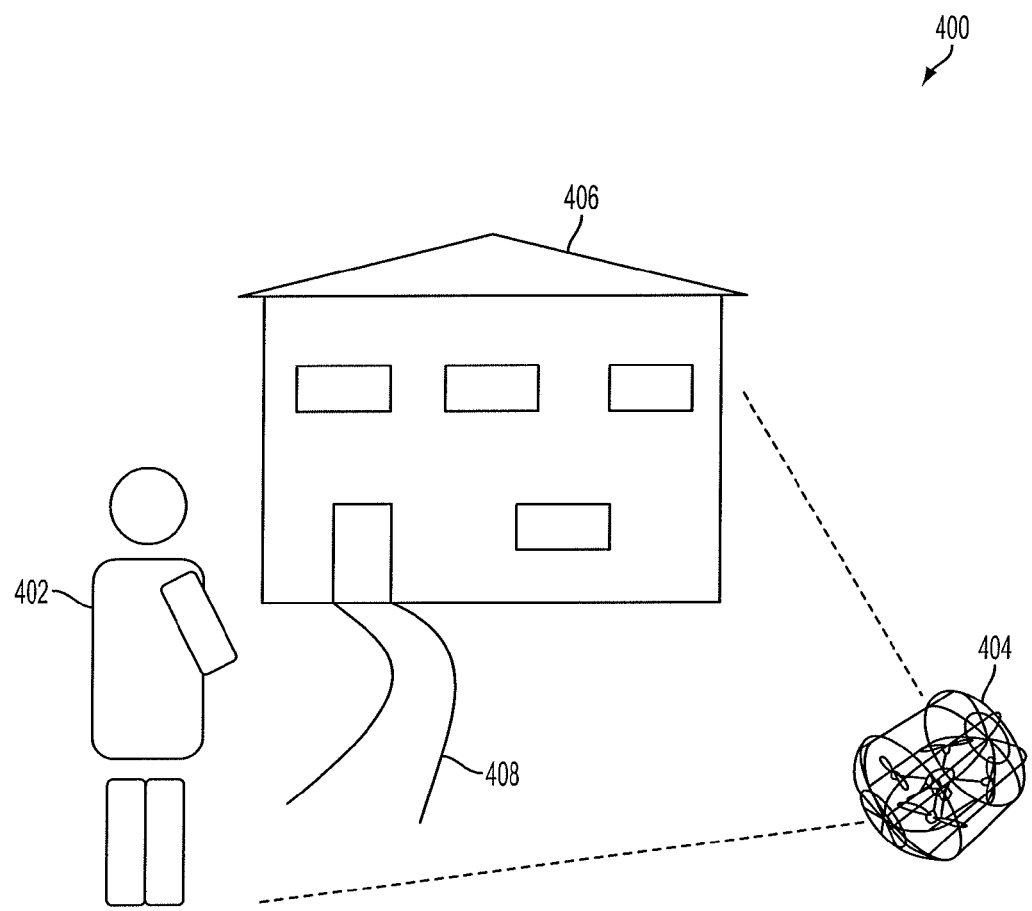
FIG. 4 illustrates a computer-based method/system of actively and automatically providing guidance to a user using a robotic device/platform configured to stay within a proximity of the user according to an embodiment of the present invention.

Referring to FIG. 4, the method/system 400 may be coupled to or embedded in a mobile mechanism such as a robotic device/platform 404 capable of flight and/or ground maneuvering within a proximity of the user 402, thereby staying within a proximity of the user 402 to detect first and/or second detected data regarding the user 402, a person, object, place or other matters within a proximity of the user 402. In another embodiment, both flight and ground maneuvering mechanisms (e.g., using a rolling mechanism such as wheels) may be implemented such that the method/system 400 can choose which of the flight or ground maneuvering mechanisms is more appropriate in the particular circumstances, for example, based on instructions received from the processor 102 or a controller in communication with or coupled to the processor 102, necessity, energy requirements, the environment within the proximity of the user 402, the type of path to the destination, the obstacles on the paths to the desired destination, or combinations thereof.

In one embodiment, due to energy consumption concerns of a flight mechanism, design preferences, implementation issues, cost, and other concerns, an automatic driving or ground maneuvering mechanism may be implemented in lieu of the flight mechanism.

As such, the mobility function may be implemented such that the method/system 400 may be moved around an object or the user 402 to provide more first and/or second detected data within a distance of the user 402. For example, if facial recognition is not possible given the current location and positioning of the robotic device/platform 404, the method/system 400 can direct ground maneuvering and/or flight mechanisms to position the sensors 106 in a better location and/or position for detecting the facial features of the person.

The flight mechanism may utilize quadrotor dynamics of spinning rotors. Such quadrotor technology or similar UAV technology may be utilized indoor and outdoor. A controller coupled to, or in communication with the processor 102 may actively and automatically control the tilting angle and the speed of the spinning rotors along with the pitch, roll, and yaw movements of the quadrotor.

In one embodiment, the processor 102 or the controller confines the maneuvering of the robotic device/platform 404 to an environment within a proximity of the user 402. As such, based on the sensed location of the user 402, position, velocity, acceleration, jerk, and snap may be controlled by a controller to maintain the quadrotor within a proximity of the user 402. The processor 102 and/or the controller may consider the blade tip speed, the lift, inertia, and linear and angular acceleration in order to monitor and control the flight operation.

Position of static or dynamic obstacles within the path of the quadrotor may also be examined. The quadrotor may perform various maneuvers of hovering, building momentum, changing orientation, and the like in order to survey or explore the environment within the proximity of the user 402 in order to increase the quantity of or improve the quality of the first detected data and/or the second detected data. The motion of the quadrotor may be controlled by changing the torque load and thrust/lift characteristics. For example, motor commands may be submitted to the quadrotor approximately 500 times a second. The quadrotor may maintain a stable flight within inches of an obstacle. The quadrotor may be equipped with the sensors 106 (e.g., the camera and laser scanners) to assist in building a map of the environment within a proximity of the user 402. The quadrotor may update the map approximately in real time. The controller or the processor 102 may populate the map by relocation of the quadrotor towards a destination about which the least first and/or second detected data are detected.

The robotic device/platform 404 may guide the user 402 towards a desired destination. For example, the robotic device/platform 404 may move to a position in front of the user 402 such that the user 402 may follow the mobile device. For example, the robotic device/platform 404 may determine based on the first detected and/or second detected data that the user 402 seeks to reach the home 406 of the user 402. The robotic device/platform 404 may assist the user 402 by outputting information helpful for guiding the user 402 on the path 408 towards the home 406 of the user 402.

Figure 5:
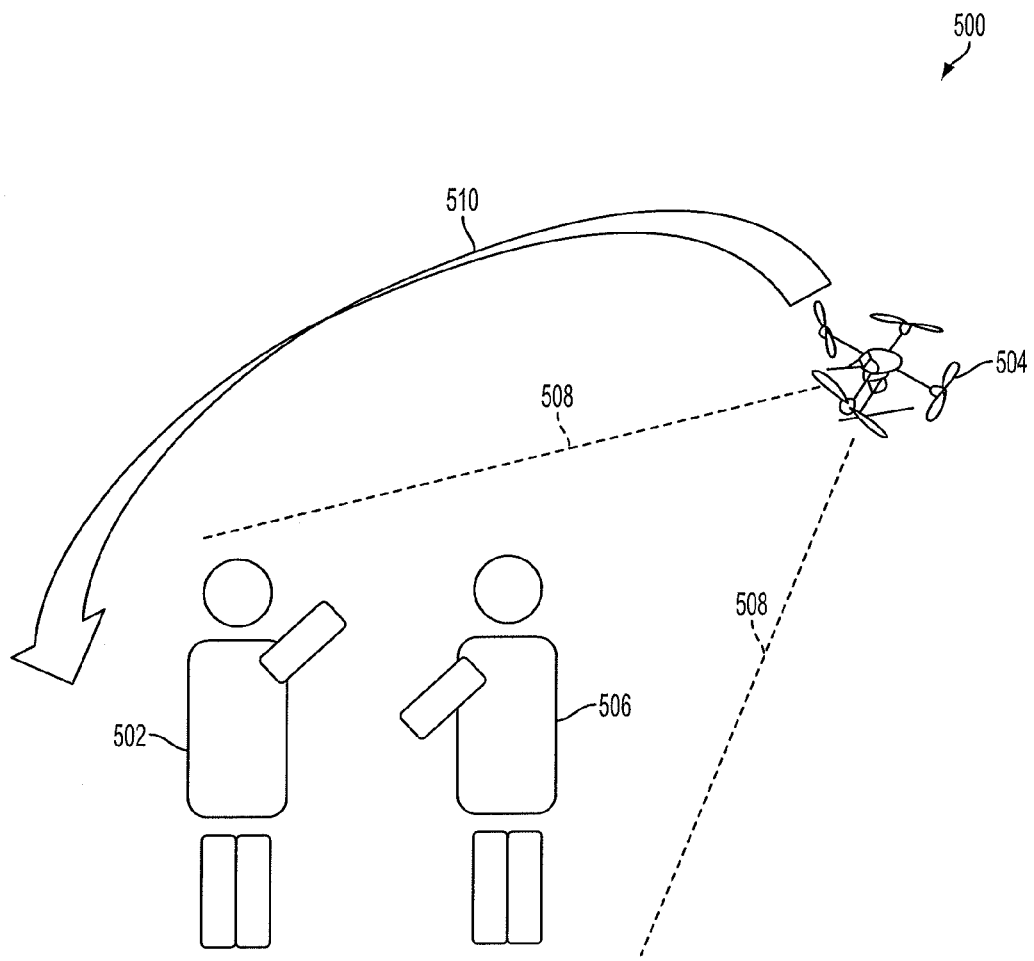
FIG. 5 illustrates a computer-based method/system of detecting and processing conversations and events within a proximity of a user, and actively and automatically providing guidance to the user according to an embodiment of the present invention.

Referring to FIG. 5, the method/system 500, the robotic device/platform 504 can maneuver on the path 510 to position the robotic device/platform 504 closer to the user 502 and/or the person 506 with whom the user 502 is having a conversation, in order to utilize the sensors 106 (e.g., the microphone) to detect a first detected data regarding the conversation between the user 502 and the person 506. The processor 102 can parse and analyze the conversation and interaction, and store relevant elements in the database 112. An image or video of the person 506 may be captured using a camera and processed as described above with respect to steps 302-322 of FIG. 3. A first and/or second output data may be outputted using the process described above with respect to the method/system 300.

Figure 6:
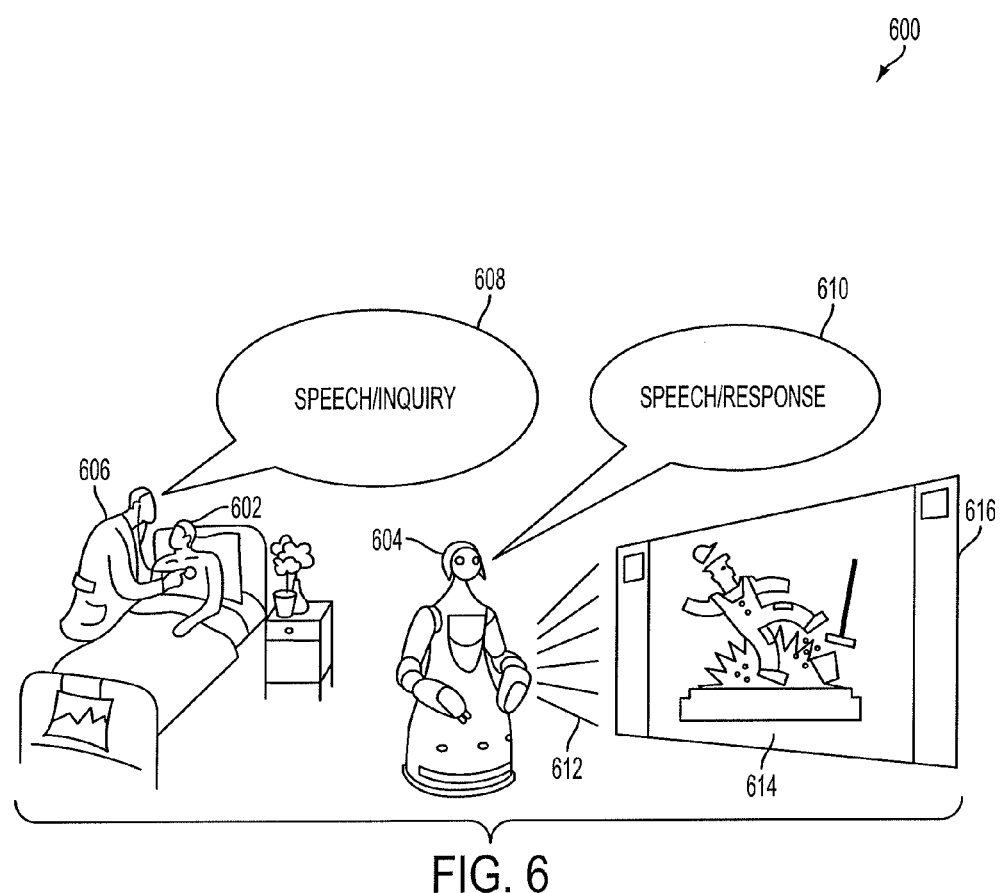
FIG. 6 illustrates a computer-based method/system of providing guidance to a user using a robotic device/platform according to another embodiment of the present invention.

Referring to FIG. 6, in the method/system 600, a robotic device/platform 604 may provide personal assistance to the user 602 when visiting a health professional 606 for consultation, diagnosis, or treatment. As with other social encounters described herein, for example, if the processor 102 determines that the user 602 may not recall certain information with respect to the health professional 606, the visitation, or other associated information, the robotic device/platform 604 may output a second output data for informing the user 602 accordingly (if appropriate under the circumstances). For example, the processor 102 may output a second output data reminding the user 602 of the number of years that the user 602 and the health professional 606 have known each other and their previous encounters, if the robotic device/platform 604 determines that outputting such information would be appropriate under the circumstances.

An important aspect of the method/system 600 is that the first output data and/or the second output data may be based on privacy concerns of the user 602 (e.g., concerns of the user 602 regarding with whom, to what extent, and in what manner the user 602 would be comfortable in sharing such a particular set of information under the current circumstances). Privacy concerns may be programmed in the form of a pre-programmed algorithm stored in the database 112 which may further be supplemented during operations of the method/system 600 based on the learned data. Such privacy concerns may be based on combinations of previously detected, processed, and stored first and/or second data or a pre-programmed algorithm for determining what type of information is appropriate to be outputted under the circumstances. In one embodiment, individuals may be distinguished in part by social interaction classes. For example, privacy concerns are less weighty when a conversation is with the health professional 606, a family member or a therapist as discussed above. As such, some of the standards as to the extent of the interaction with a trusted individual can be stored in the pre-programmed algorithm, and some of the information regarding with whom and to what extent the method/system 600 should interact can be adjusted based on the first detected data and the second detected data.

In one embodiment, the method/system 600 may associate a high level of trust with a person based on prior detected conversations of the user 602 with the person. That is, a detected friend having close/intimate relations with the user 602 can be distinguished from an acquaintance or a stranger based on prior conversations and interactions. Based in part on the recognized distinction, the robotic device/platform 604 may adjust the degree and the type of information included in the second output data. For example, if the robotic device/platform 604 determines that because the user 602 would be comfortable with sharing certain information with the health professional 606 (acting in a professional capacity with expectations of upholding the privacy of the user 602), the robotic device/platform 604 would output a higher degree of or more private information than the robotic device/platform 604 would if the interactions were directed to an individual encountered for the first time and not acting in a confidential and professional capacity. The method/system 600 can determine whether the detected person is a health professional 606, therapist, or other professionals endowed with high level of trust and expectation of upholding privacy of communications based on the detected first and/or second data, pre-programmed algorithm, and previously detected, processed, and stored first and/or second data as discussed above with respect to FIG. 3.

In one embodiment as shown in FIG. 6, for example, the health professional 606 may inquire about the reason, the timing, or the cause of an arm injury sustained by the user 602 which has prompted visiting the health professional 606 by posing the speech/inquiry 608 to the user 602. The speech/inquiry 608 may be "How and when did your arm get injured?" directed to the user 602. The robotic device/platform 604 may parse and analyze the conversation as described above in order to analyze the elements of the speech/inquiry 608 and the relationship, sequence, or correlation of the elements to one another based on previously detected, processed, and stored first and/or second data. The robotic device/platform 604 may search the database 112 regarding previous injuries sustained. The robotic device/platform 604 may match the elements of "arm" and "injury" with a slip and fall accident leading to an arm injury which was sustained during a prior week and catalogued accordingly. After analyzing the elements of the speech/inquiry 608, the robotic device/platform 604 may determine that the health professional 606 is interested in learning about the injury and that disclosing such information via the second output data would be appropriate in the current circumstances. The robotic device/platform 604 may actively and automatically output a second output data informing the health professional 606 and the user 602 regarding the injury. For example, the robotic device/platform 604 may generate an output speech/response 610 indicating that "[name of user 602] slipped last week landing on his arm. Here is how it happened." The output speech/response 610 may further include details regarding the recorded event (i.e. accident) in order to output a second output data for providing proactive assistance for an improved diagnosis and/or for providing a reminder data of when and how the injury occurred.

The robotic device/platform 604 may output a first output data and/or a second output data via the output device 114 or various other devices or methods without limiting the scope of the present invention. For example, the robotic device/platform 604 may output a second output data using the communications unit 104.

In one embodiment, the robotic device/platform 604 may be equipped with a projector or a projection 612 capable of projecting an output image/video 614 as determined by the processor 102. For example, the robotic device/platform 604 may have previously recorded the slip and fall accident leading to the arm injury when the accident occurred. If so, the robotic device/platform 604 may output the second output data displaying the output image/video 614 on the wall/screen 616 in order to provide assistance for the diagnosis, treatment, or consultation. In other embodiments, the second output data may be communicated to another device of the user 602 or the health professional 606 (e.g., a handheld communication device). In yet another embodiment, the robotic device/platform 604 may include a communications interface capable of communicating the information to the user 602 and/or the health professional 606.

The source of the first detected data and/or the second detected data may not necessarily be the sensors 106. That is, multiple storage units and electronic devices may operate in concert sharing information in order to improve the quality and increase the quantity of information on which the outputted data are based. For example, the robotic device/platform 604 may have access to the Internet or be in communication with the cloud-based database and computing 110 to receive input data previously stored by an external device (e.g., smart phone) of the user 602. For example, if the user 602 has previously stored data in any of the electronic devices in communication with the cloud-based database and computing 110, the robotic device/platform 604 may search such previously stored data for relevant information regarding the arm injury and output a second output data as described above accordingly.

Figure 7:
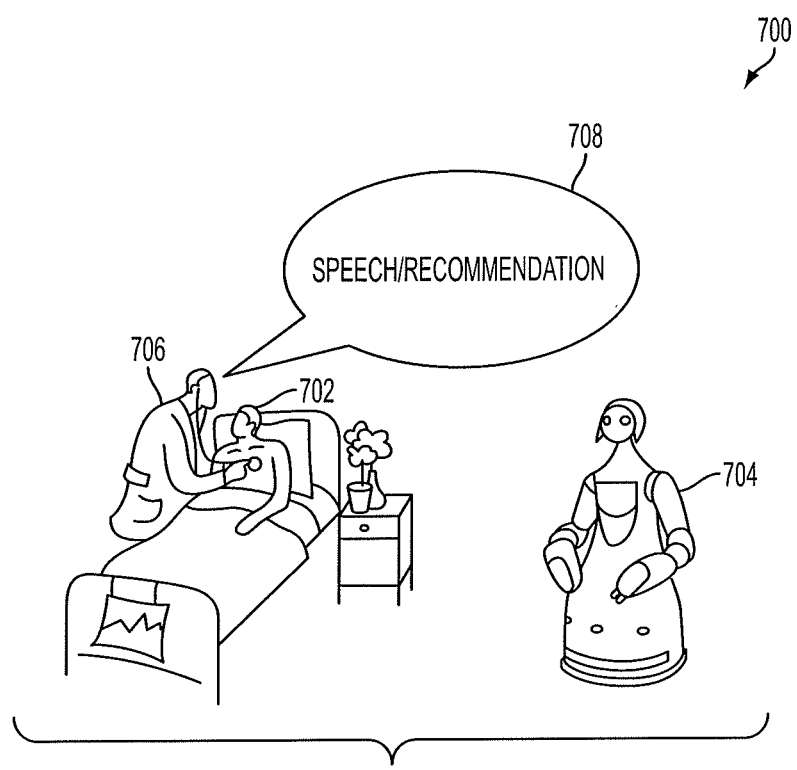
FIG. 7 illustrates a computer-based method/system of actively and automatically analyzing, and storing the first and/or second detected data using a robotic device/platform according to an embodiment of the present invention.

Referring to FIG. 7, in one embodiment of the method/system 700, the robotic device/platform 704 may be the robotic device/platform 604 discussed above with respect to FIG. 6. For example, the health professional 706 intends to provide recommendations as to courses of action that would improve a health condition of the user 702. For example, the health professional 706 may utter the speech/recommendation 708, stating that "I see how you got injured. Please maintain a nutritious diet including protein and vegetables, and perform weekly exercise/physical therapy routines of A, B, and C using 10 pound free weights." The processor 102 of the robotic device/platform 704 analyzes the elements of the speech/recommendation 708. The method/system 700 stores and catalogues the information relating to exercise/physical therapy routines of A, B, and C using 10 pound free weights and the robotic device/platform 704 and recognizes that the exercise/physical therapy routines of A, B, and C have to be performed once a week as instructed. The method/system 700 may automatically schedule reminders in the database 112 to be outputted on a weekly basis. The method/system 700 further stores and catalogues the analyzed data (e.g., regarding the recommended dietary regimens) in the database 112.

Figure 8:
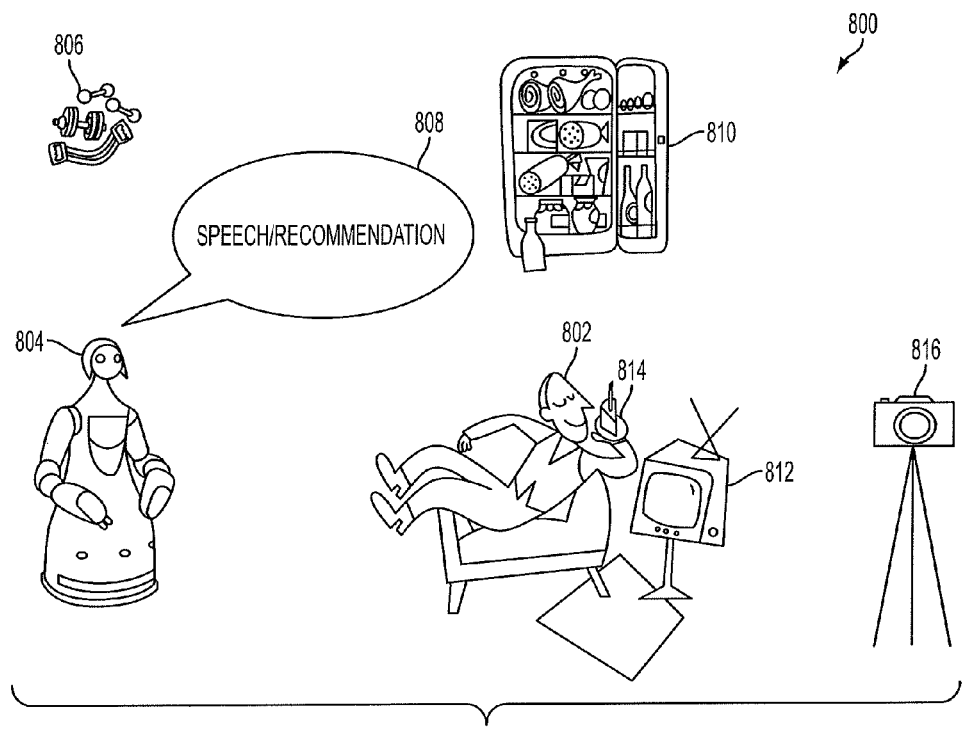
FIG. 8 illustrates a computer-based method/system of actively and automatically outputting, using a robotic device/platform, second output data for providing personal assistance regarding health concerns to a user according to an embodiment of the present invention.

Referring to FIG. 8, in one embodiment of the method/system 800, the robotic device/platform 804 may be the robotic device/platform 704 discussed above with respect to FIG. 7. The robotic device/platform 804 may recommend, motivate, or remind the user 802 of the information collected as discussed above with respect to FIGS. 6 and 7. For example, the method/system 800 may analyze the first detected data and/or the second detected data in order to determine whether the user 802 is complying with the dietary and physical therapy guidelines set forth in the speech/recommendation 708.

For example, based on the analyzed first and second detected data, the method/system 800 may determine that the user 802 has only performed physical exercise routine A during the past week. The method/system 800 may further determine that the user 802 is watching the TV 812 and eating a certain type of food 814 (e.g., a cheesecake) using various object recognition detection and processing methods and systems. The method/system 800 may further recognize that the user 802 is currently resting on the couch, and has not performed a substantial degree of physical activities during the past week.

The method/system 800 may search the Internet, the cloud-based database and computing 110, the memory 108, or other data to determine the nutritional value of the food 814. For example, the method/system 800 may output the output speech/recommendation 808 in order to encourage the user 802 to undertake a healthier food choice in order to facilitate a faster recovery based on the recommendations of the health professional 706. The method/system 800 may further seek to motivate the user 802 to perform the physical therapy routines of B and C. The output speech/recommendation 808 may be "A week has passed since you last performed physical therapy routines B and C. You can use the light weights in the room per health professional's instructions. There are vegetables and eggs in the fridge to help maintain a nutritious diet." In another embodiment, the robotic device/platform 804 may further remind the user 802 of taking medication properly if the health professional 706 had prescribed medication and provided instructions for taking the medication.

In other embodiments, the method/system 800 may be coupled to or in communication with a pedometer or other systems providing health information in order to have access to additional information regarding the health of the user 802. Alternatively, the method/system 800 may determine health factors based on the first detected and/or second detected data corresponding to exercise activities, dietary habits, and other matters with or without an external health monitoring device.

Figure 9:
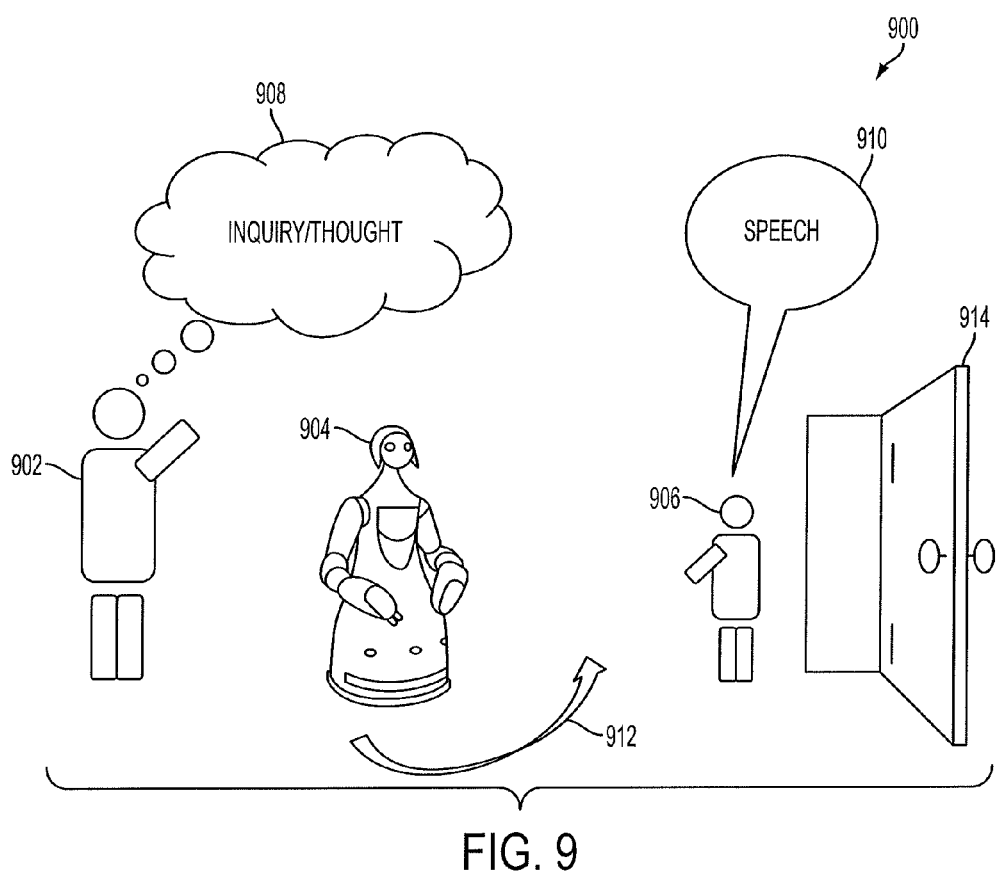
FIG. 9 illustrates a computer-based method/system of actively and automatically providing personal assistance to a user with memory retention/retrieval difficulties using a robotic device/platform according to an embodiment of the present invention.

Referring to FIG. 9, in the method/system 900, the user 902 may suffer from Alzheimer's complications or dementia, or alternatively, the user 902 may have certain difficulties with retaining, retrieving, or analyzing information using human brain/memory. The method/system 900 may recognize that the user 902 is suffering from such complications based on the pre-programmed algorithm and/or detected data. In one embodiment, the method/system 900 may implicitly provide information that is appropriate under the circumstances in order to jog the memory of the user 902. For example, a robotic device/platform 904 may be continuously traversing an environment within the proximity of the user 902 and analyzing the first detected data and/or the second detected data in order to determine if a new object, person, living being, or other matter has entered the environment.

For example, as shown in FIG. 9, the robotic device/platform 904 may recognize, using the detected data from the sensors 106, that a person has entered the environment by opening the door 914. The robotic device/platform 904 may move along the path 912 to position at least one of the sensors 106 in a better position to detect a first detected data and/or a second detected data regarding the newly entered person 106. The user 902 may utter the inquiry/thought 908 of "Who is that? He looks familiar." If the user 902 does not utter the inquiry/thought 908, the method/system 900 may recognize that the user 902 has not identified the newly entered person 906. For example, the processor 102 of the robotic device/platform 904 may utilize a camera to operate face recognition of at least a facial feature of the user 902 to determine that the user 902 is perplexed while attempting to identify the newly entered person 906. In another embodiment, the method/system 900 may automatically output the second output data to jog the memory of the user 902 in a subtle manner as described below. Such an embodiment may be set as a default mode of operation if the robotic device/platform is aware that the user 902 may have difficulties in retaining or retrieving information from memory.

For example, the processor 102 of the robotic device/platform 904 may utilize a camera to operate face recognition of at least a facial feature of the newly entered person 906. The method/system 900 may recognize that the newly entered person 906 is Michael, the nephew of the user 902. In another embodiment, the recognition of the identity of the user 902 may be through speech recognition and the source of the speech (e.g., using a 3-D microphone). For example, if the newly entered person 906 utters a speech 910, the processor 102 may determine the identity of the newly entered person 906 and look up prior relevant data regarding the newly entered person 906 using the method/system 300. Other characteristics, interactions, physical appearance, or the like may be analyzed in order to determine the identity of the newly entered person 906.

The processor 102 may take into account the reliability of a particular piece of information detected by one of the sensors 106. For example, for identification or recognition of the newly entered person 906, the processor 102 may assign various probabilities of accurate detection or recognition. For example, the assigned probabilities of accurate detection or recognition may be based on the mechanism used to detect the newly entered person 906. For example, recognition or identification of the newly entered person 906 based on an identity code programmed in an identity device (e.g., a cellular phone) of the newly entered person 906 may not be as reliable as recognition based on a facial feature of the newly entered person 906 using a camera or speech recognition using a microphone, given that the newly entered person 906 could be carrying an identity device of another individual.

The assigned probabilities of accurate identification or recognition may be further based on the circumstances under which the first detected data and/or the second detected data are detected. For example, if a camera is obstructed causing the face of the newly entered person 906 to be unrecognizable, the method/system 900 may assign a relatively low probability of accurate detection or recognition in identifying the newly entered person 906. If the obstruction is removed and a facial recognition processing mechanism confirms the identity of the newly entered person 906, a higher probability of confidence would be associated with the identification or recognition. As such, the processor 102 may identify or recognize the newly entered person 906 based on a combination of various instances of data detection and further based on the corresponding probabilities of accurate recognition or identification.

Referring to FIG. 9, when the method/system 900 determines that the newly entered person 906 is "Michael," a nephew of the user 902, the robotic device/platform 904 outputs appropriate information to provide indirect, subtle and implicit reminders to the user 902. For example, if the method/system 900 recognizes that the newly entered person 906 is a close relative, the processor 102 of the robotic device/platform 904 may determine that outputting information regarding the last time that the newly entered person 906 and the user 902 have met would not be appropriate in the current circumstances. Instead, the method/system 900 may provide information in a subtle fashion to remind the user 902 that the newly entered person 906 is the nephew of the user 902. For example, the robotic device/platform 904 may direct an output speech 916 (not shown) to the newly entered person 906, stating that "Hello Michael, your uncle [name of the user 902] will be with you shortly," thereby indirectly providing a reminder to the user 902 in a subtle fashion as appropriate under the circumstances.

Alternatively or in addition, the user 902 may request the robotic device/platform 904 to generate additional information. The robotic device/platform 904 may passively output, using the communications unit 104, a first output data upon the request from the user 902.

Figure 10:
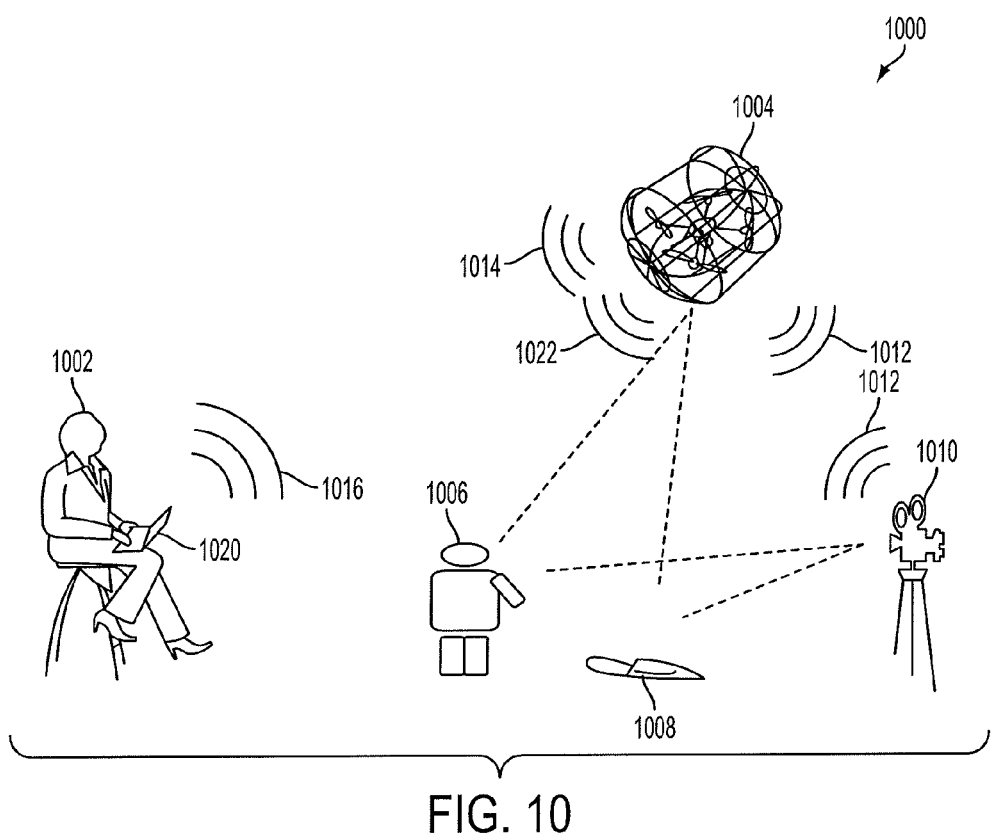
FIG. 10 illustrates a computer-based method/system of providing parental control assistance and/or attempting to decrease the likelihood of harm from a hazardous object, activity or event, using a robotic device/platform according to an embodiment of the present invention.

Referring to FIG. 10, the method/system 1000 may assist a parent/caregiver 1002 in performing parental control or supervision with respect to the child 1006. The method/system 1000 may further seek to distance the child 1006 from hazardous conditions, objects, or events.

Stored parental control data may provide guidelines for the processor 102 to analyze an action, speech, or interaction of the child 1006, characteristic of an object or occurrence of an event, or combinations thereof. The stored parental control data may be based on input received from a parent/caregiver 1002, previously detected, processed, and stored first and/or second data, or a pre-programmed algorithm stored in the database 112. The processor 102 may selectively supplement the parental control data stored in the database 112 based on the first detected data and/or second detected data. The processor 102 may utilize the parental control data to determine whether to flag an action, speech, interaction of the child 1006, characteristic of an object near the child 1006, occurrence of an event, or combinations thereof which may assist the parent/caregiver 1002 in parental control tasks or supervision. For example, during normal daily activities, the method/system 1000 may have access to data regarding the homework or tasks that the child 1006 is expected to perform. The processor 102 may analyze the actions of the child 1006 based on the stored parental control data. The processor 102 may determine whether the actions of the child 1006 are in compliance with the homework or tasks. The robotic device/platform 1004 may report a daily summary of activities of the child 1006 to the parent/caregiver 1002 based on the analyzed actions of the child 1006.

For example, the robotic device/platform 1004 may output a second output data via a communications mechanism 1022 to remind, encourage or motivate the child 1006 to perform certain homework or tasks. The communications mechanism 1022 may be speech generated via a speaker of the communications unit 104 intended to encourage the child 1006 to perform the required homework or tasks. The robotic device/platform 1004 may alternatively or in addition, display an output image/video intended to convey the second output data to the child 1006. In one embodiment, the summary is reported in real time, in intervals, on a daily basis or during other time periods to the parent/caregiver 1002 via the communications mechanism 1014 or other output devices or mechanisms. For example, the communications mechanism 1014 may be a generated signal received as signal 1016 by a portable electronic device 1020 used by the parent/caregiver 1002. Data included in the report may be based on the first detected data and/or the second detected data regarding an environment within a proximity of the child 1006.

The method/system 1000 may further be in communication with an external device that supplements the detected data. For example, an off-board camera 1010 may be utilized to provide an additional vantage point for observing the activities of the child 1006. For example, a security camera that is in communication with the network that the method/system 1000 is connected with can observe the child 1006 when the child 1006 is positioned in view of the security camera. The robotic device/platform 1004 may further be configured to follow or stay within a proximity of the child 1006 to improve detection of the first detected data and/or the second detected data regarding an environment within a proximity of the child 1006.

In another embodiment, the method/system 1000 is able to detect hazardous conditions, events, or objects (e.g., a sharp object 1008 within a proximity and within reach of the child 1006). The processor 102 of the robotic device/platform 1004 may warn the child 1006 via outputting a second output data. For example, the robotic device/platform 1004 may generate a speech, sound or voice stating that "please stay away from the knife. It's very dangerous." Alternatively or in addition, the robotic device/platform 1004 may engage the attention of the child 1006 in order to distract the child away from the sensed hazardous object (the sharp object 1008). For example, the method/system 1000 may output a reference to a toy or attractive activity in the vicinity of the child 1006, play a song, and display an output image/video via the output device 114, or the like to direct the child 1006 away from the detected hazardous object (the sharp object 1008).

The method/system 1000 may detect hazardous conditions that may inflict harm upon the child 1006. As used herein, the term "hazard" includes any hazard, defect, obstacle, flaw, and other abnormalities that exist in any environment within the proximity of the child 1006.

The hazard detection algorithm of the method/system 1000 may be modified to be applied to an adult person. The hazardous conditions, events, or objects may be different depending on the user. For example, for users with poor vision or using a wheelchair, a hazard may comprise detection of steps, a steep incline, a narrow hallway, a bumpy path, and the like. In other circumstances a hazard may comprise a handrail that is not properly secured to a building or support, a weed growing up through a crack in the sidewalk, road construction, a leaking pipe which creates a puddle, an impediment to rate of travel, an impediment to safety, a nuisance, a strain on travel, a pothole in the sidewalk, a wet floor due to a spill, a low hanging branch on a path, and any other hazardous event or matter with likelihood of inflicting physical or psychological harm or discomfort. The communications unit 104 may output the second output data to provide warnings or recommendations accordingly.

Figure 11:
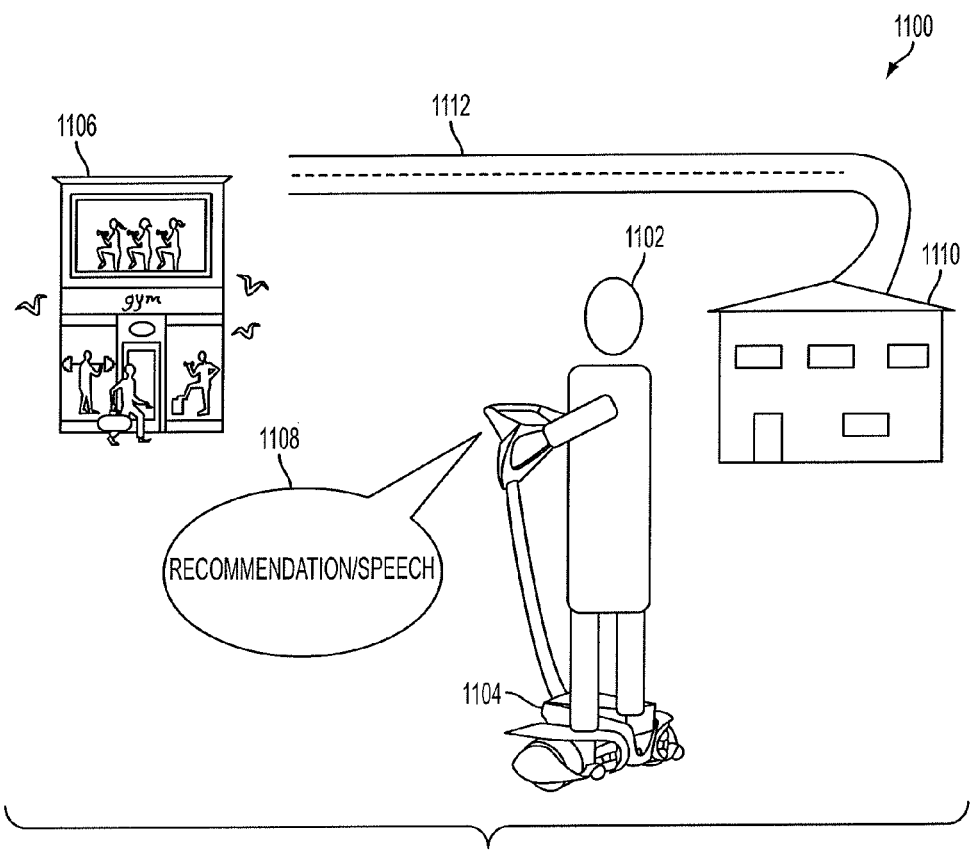
FIG. 11 illustrates a computer-based method/system of providing personal assistance using a robotic device/platform according to an embodiment of the present invention.

Referring to the method/system 1100 of FIG. 11, in one embodiment, the robotic device/platform 1104 may be a two-wheeled self-balancing device. The user 1102 may shift his/ her weight in order to direct the robotic device/platform 1104 to maneuver towards a desired direction. The handle bar of the robotic device/platform 1104 may be included solely for providing additional comfort for the user 1102 given that the detected weight shift of the user 1102 using the base portion 1114 of the robotic device/platform 1104 may contain sufficient maneuvering directions from the user 1102.

In one embodiment, the robotic device/platform 1104 may communicate directly with the user 1102. For example, the robotic device/platform 1104 may have speech recognition and generation capabilities as discussed above. For example, a camera may be implemented on the robotic device/platform 1104 to capture the first detected data and/or the second detected data regarding the surrounding environment of the user 1102. In another embodiment, the user 1102 may communicate with a handheld device of the user 1102 (e.g., a smart phone) in communication with or coupled to a communication port of the robotic device/platform 1104. For example, a software application may be installed on a smart phone of the user 1102 in order to communicate data with the robotic device/platform 1104.

As shown in FIG. 11, the method/system 1100 has determined, based on the detected, processed, and stored data that the user 1102 seeks to perform physical activities and exercises in order to maintain a healthier lifestyle. The method/system 1100 may include or be in communication with a GPS device. The method/system 1100 may recognize that a building is located on the right hand side of the user 1102. The method/system 1100 may automatically obtain data regarding the building and determine that the building is a gymnasium 1106. The data may be obtained from the combination of data received from the GPS device and previously detected, processed, and stored first and/or second data. The method/system 1100 may further determine the location of the home 1110 of the user 1102 and the distance and directions from the home of the user 1102 to the gymnasium 1106. The method/system 1100 may automatically output a second output data recommending that the user 1102 consider signing up at the gymnasium 1106.

The method/system 1100 may determine that based on the driving directions obtained from the GPS device, the route will take 20 minutes by travelling via the robotic device/platform 1104 and will take 4 minutes by travelling via an automobile on the road 1112. In order to facilitate the decision making process, the method/system 1100 may provide further information, for example, by generating the following output recommendation/speech 1108: "Since you mentioned that you seek to work out to lose weight, I have noticed that a gym has opened on your right recently. If you use this device, it will take you 20 minutes and if you drive westbound using road 1112, it will take you 4 minutes to get there. It may be a good idea to exercise in the morning before work."

Figure 12:
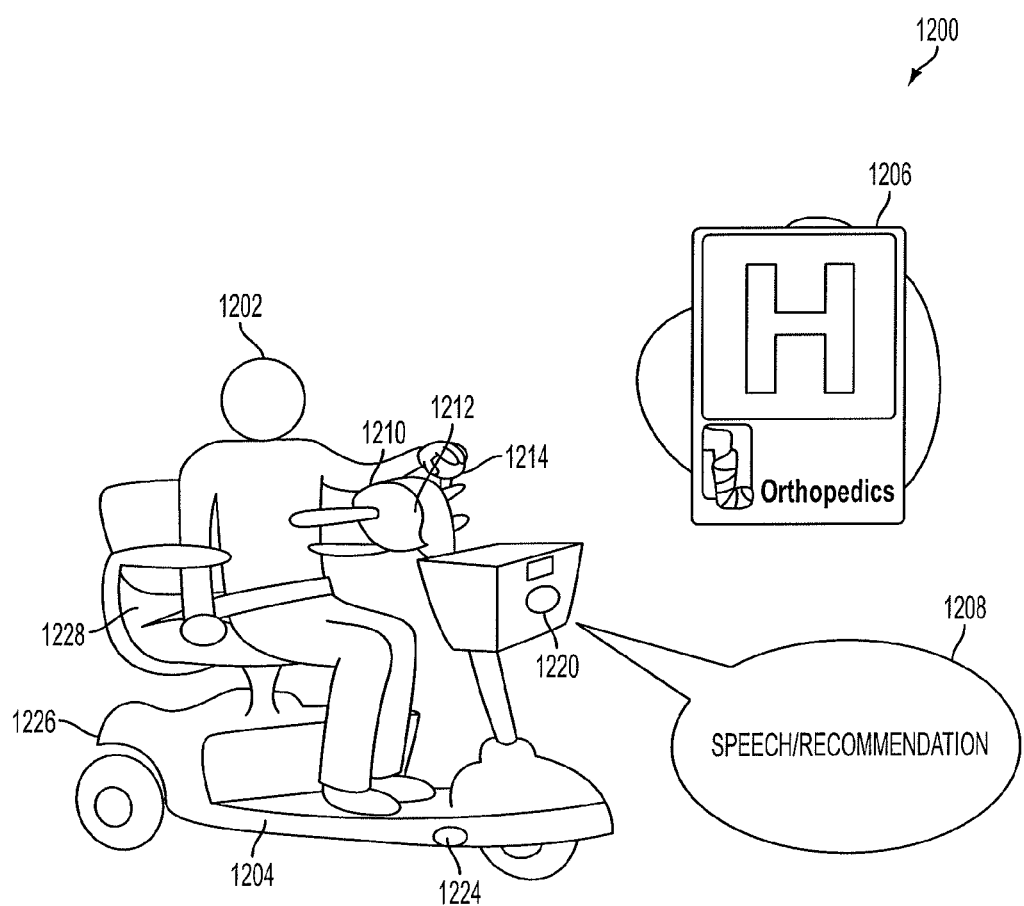
FIG. 12 illustrates a computer-based method/system of providing personal assistance using a robotic device/platform according to an embodiment of the present invention.

Referring to the method/system 1200 of FIG. 12, a robotic device/platform 1204 may be a wheelchair or a three-wheeled transportation device. Any of the sensors 106 described above may be implemented on the robotic device/platform 1204. For example, the sensors 106 may be installed in sensor locations 1210, 1220, 1224, and 1226. The sensors 106 may be positioned at any other portion of the robotic device/platform 1204 without limiting the scope of the invention. For example, a camera may be positioned at the sensor location 1220 in order to collect data regarding the surrounding environment. A camera, microphone, or other sensors 106 described above may also be installed at a sensor location 1210. Perimeter monitoring sensors and laser scanning sensors may be installed as sensor locations 1224 and 1226. IMU's, gyroscopes, GPS system, and the like may further be mounted on the robotic device/platform 1204. The robotic device/platform 1204 may further include a user interface 1212 to communicate with the user 1202.

The output device 114 of the robotic device/platform 1204 may be a mechanical device having actuators capable of maneuvering the robotic device/platform 1204 based on a third output data received from the processor 102. For example, the robotic device/platform 1204 may include a joystick 1214 that allows the user 1202 to maneuver the robotic device/platform 1204 towards a desired direction. Alternatively or in addition, tactile data of the user 1202 may be detected.

For example, in the case of an Alzheimer's patient or a user 1202 with short term memory difficulties, if the user 1202 forgets a particular destination, the method/system 1200 may guide the wheelchair and the user 1202 to the destination. If the user 1202 is controlling the method/system 1200, e.g., using the joystick 1214 as described above, a response such as a vibration may be output to alarm the user 1202 that the user 1202 is heading the wrong way or to further guide the user 1202 towards the desired destination. Vibration motors can further provide feedback to the user 1202. Such vibration motors can be integrated in or coupled to an article of manufacture carried or worn by the user 1202. For example, a belt 1228 or a vest may be coupled to the robotic device/platform 1204 by which a vibration may provide information to the user 1202.

Using the sensors 106, the method/system 1200 may recognize that an orthopedic clinic 1206 is located on the left of the robotic device/platform 1204 and the user 1202. Using the process described in details above (e.g., with respect to method/system 300 of FIG. 3), the method/system 1200 may match the second detected data regarding the observed orthopedic clinic 1206 with a previously stored event (e.g., an arm injury discussed with respect to FIG. 6). Using the process described above with respect to FIG. 3, the method/system 1200 may output a second output data for providing a reminder and recommending that the user 1202 visits the orthopedic clinic 1206 in order to receive treatment before the injury exacerbates. For example, the method/system 1200 may output an output speech/recommendation 1208 as follows: "You can visit the Orthopedic Clinic on your left for the arm injury you sustained last week."

Referring to FIGS. 1-12, one aspect of the invention is that information can be shared between all or various combinations of the devices set forth above in FIGS. 1-12. For example, the robotic devices/platforms 204, 404, 504, 604, 704, 804, 904, 1004, 1104, and 1204 discussed with respect to FIGS. 2, 4, 5, 6, 7, 8, 9, 10, 11, and 12, and external devices such as communication devices, cell phones, laptops, cameras, or other devices capable of communicating with or being coupled to the listed devices or units can share information, using the cloud-based database and computing 110 or the Internet, in order to access, store, and process the pool of the first and/or second detected, processed, and stored data.

Figure 13:
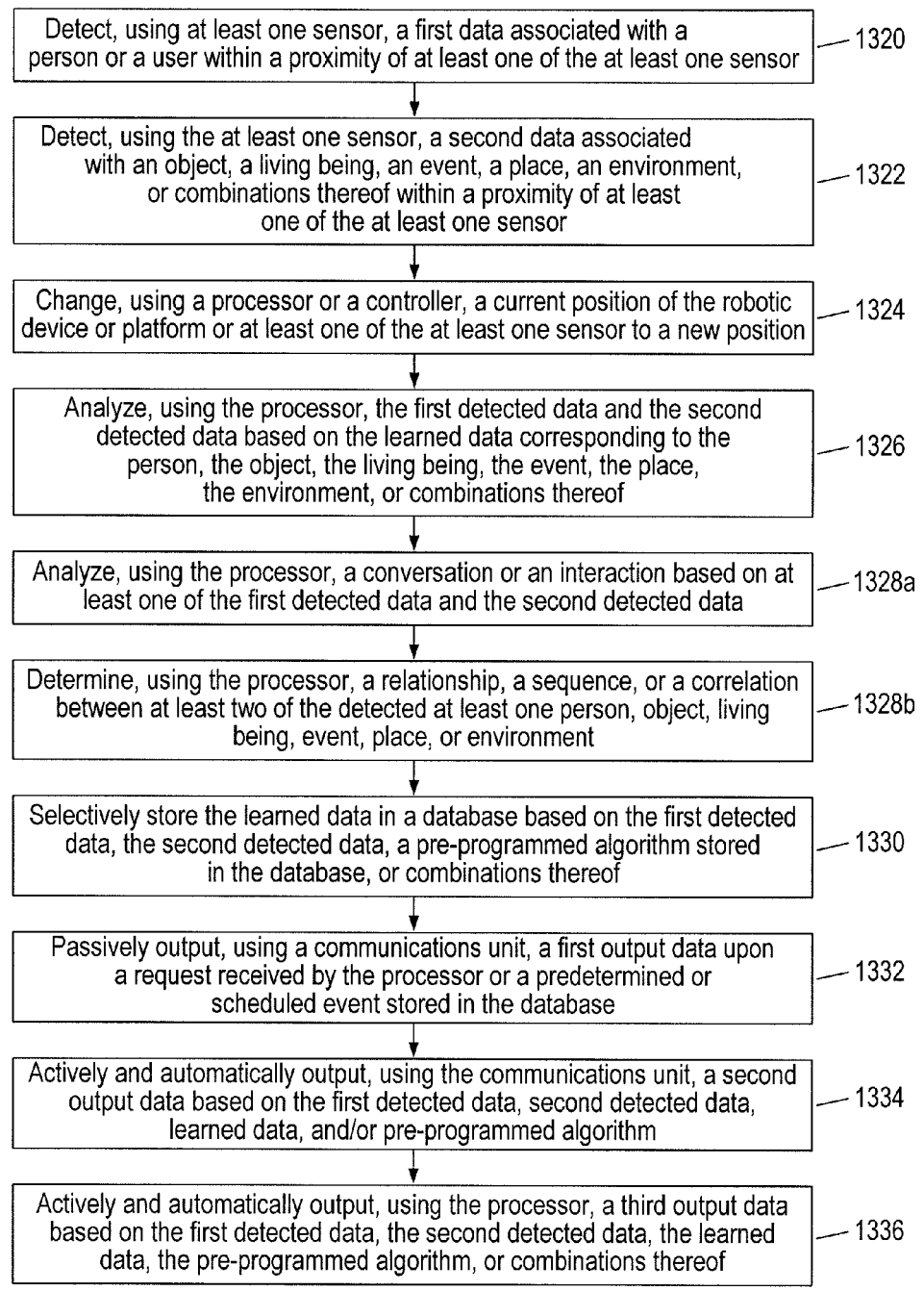
FIG. 13 illustrates a flowchart diagram showing a computer-based method of outputting first, second, and/or third output data based on the first detected data and the second detected data according to an embodiment of the present invention.

FIG. 13 illustrates a decision flowchart diagram showing a computer-based method 1300 of outputting first, second, and/or third output data. Referring to step 1320, a first data associated with a person or a user within a proximity of at least one of the at least one sensor is detected using the at least one sensor (e.g., sensors 106). Referring to step 1322, a second data associated with an object, a living being, an event, a place, an environment, or combinations thereof within a proximity of at least one of the at least one sensor is detected. In step 1324, a current position of the robotic device or platform or at least one of the at least one sensor (e.g., sensors 106) is changed to a new position, for example, such that the robotic device or platform continuously stays within a proximity of a user as the user moves to various positions. In step 1326, the first detected data and the second detected data are analyzed by the processor 102 based on the learned data corresponding to the person, the object, the living being, the event, the place, the environment, or combinations thereof.

In step 1328a, a conversation or an interaction is analyzed by the processor 102 based on at least one of the first detected data and the second detected data. In step 1328b, a relationship, a sequence, or a correlation may be determined between at least two of the detected at least one person, object, living being, event, place, or environment. In step 1330, the learned data are stored in a database 112 based on the first detected data, the second detected data, a pre-programmed algorithm stored in the database, or combinations thereof. In step 1332, a first output data is passively outputted using the communications unit 104 upon a request received by the processor 102 or a predetermined or scheduled event stored in the database 112. In step 1334, a second output data is actively and automatically outputted, using the communications unit 104, based on the first detected data, second detected data, learned data, and/or pre-programmed algorithm. In step 1336, a third output data is outputted using the processor 102 and based on the first detected data, the second detected data, the learned data, the pre-programmed algorithm, or combinations thereof. As set forth above with respect to steps of the flowchart in FIG. 3, the steps of the method according to the present invention may be performed simultaneously or in various combinations of orders.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., android, iPhone®, Palm Pilot®, Blackberry®), cellular phone, kiosk, and the like), online communications, satellite communications, off-line communications, wireless communications, transponder communications, local area network (LAN), wide area network (WAN), virtual private network (VPN), networked or linked devices, keyboard, mouse and/or any suitable communication or data input modality. Specific information related to the protocols, standards, and application software utilized in connection with the Internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers, and other devices on demand.

Systems, methods and computer program products are provided. References to "various embodiments", in "some embodiments", "one embodiment", "an embodiment", "an example embodiment", and the like indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

The steps of a method or algorithm described in connection with the examples disclosed herein may be embodied directly in hardware, in a software module executed by the processor 102, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor 102 such that the processor 102 can read information from, and write information to, the storage medium. In the alternative, the storage medium may be integral to the processor 102. The processor 102 and the storage medium may reside in an Application Specific Integrated Circuit (ASIC).

The methods/systems 100-1300 may be described herein in terms of functional block components, screen shots, optional selections and various processing steps. It should be appreciated that such functional blocks may be realized by any number of hardware and/or software components configured to perform the specified functions. For example, the methods/systems 100-1300 may employ various integrated circuit components, e.g., memory elements, processing elements, logic elements, look-up tables, and the like, which may carry out a variety of functions under the control of one or more microprocessors or other control devices. Similarly, the software elements of the methods/systems 100-1300 may be implemented with any programming or scripting language such as, VPL, C, C++, C#, Java, JavaScript, VBScript, Macromedia Cold Fusion, COBOL, Microsoft Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the methods/systems 100-1300 may employ any number of conventional techniques for data transmission, signaling, data processing, network control, and the like.

As will be appreciated by one of ordinary skill in the art, the methods/systems 100-1300 may be embodied as a customization of an existing system, an add-on product, upgraded software, a stand-alone system, a distributed system, a method, a data processing system, a device for data processing, and/or a computer program product. Furthermore, the methods/systems 100-1300 may take the form of a computer program product on a non-transitory computer-readable storage medium having computer-readable program code means embodied in the storage medium. Any suitable computer-readable storage medium may be utilized, including hard disks, CD-ROM, optical storage devices, magnetic storage devices, and/or the like.

Exemplary embodiments of the methods/systems 100-1300 have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A computer-based method of actively and automatically providing personal assistance using a robotic device or platform having a processor coupled to at least one sensor, a communications unit, and an output device, the method comprising the steps of:
   detecting, using the at least one sensor, a first data associated with at least one person within a proximity of at least one of the at least one sensor;
   detecting, using the at least one sensor, a second data associated with an object, a living being, an event, a place, an environment, or combinations thereof within a proximity of at least one of the at least one sensor;
   selectively storing, using the processor, a learned data in a database based on the first detected data, the second detected data, a pre-programmed algorithm stored in the database, or combinations thereof;
   passively outputting, using the communications unit or the output device coupled to or in communication with the processor, a first output data upon a request received by the processor or a predetermined or scheduled event stored in the database; and
   actively and automatically outputting, using the communications unit or the output device, a second output data based on the first detected data, the second detected data, the learned data, the pre-programmed algorithm, or combinations thereof,
   wherein the step of actively and automatically outputting, using the communications unit or the output device, the second output data is performed using an item that can be worn or carried by a person.

2. The method of claim 1, wherein:
   the first detected data corresponds to a visual characteristic, a speech, tactile information, a motion, an interaction, an action, a behavior, a conversation, a characteristic, a location, an identity, an attribute, or combinations thereof associated with the at least one person,
   the second detected data corresponds to at least one of:
      a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or
      a characteristic, a type, a location, a temperature, a moisture content, a weather condition, a sound, a visual characteristic, an attribute, or combinations thereof associated with the place or the environment within a proximity of at least one of the at least one sensor.

3. The method of claim 1, further comprising:
   analyzing, using the processor, the first detected data and the second detected data based on the learned data corresponding to the detected at least one person, object, living being, event, place, environment, or combinations thereof,
   wherein the steps of selectively storing the database and actively and automatically outputting the second output data are further based on the analyzed first and second detected data.

4. The method of claim 1, wherein the robotic device or platform is configured to move on a ground surface or in an air space to stay within a proximity of a user to enable or enhance the step of detecting the first detected data and second detected data or to enable or enhance the step of actively and automatically outputting the second output data for enhancing communication with the user.

5. The method of claim 1 further comprising:
   determining, using the processor, a relationship, a sequence, or a correlation between at least two of the detected at least one person, object, living being, event, place, or environment,
   wherein the step of actively and automatically outputting the second output data is further based on the determined relationship, sequence, or correlation.

6. The method of claim 1, wherein the at least one person includes at least a child, and the pre-programmed algorithm includes a hazard detection algorithm, the method further comprising:
   determining, using the processor, a hazardous event or a hazardous object within a proximity of the child having a possibility of inflicting emotional or physical harm to the child, based on the hazard detection and analysis algorithm, the first detected data, and the second detected data,
   wherein the step of actively and automatically outputting the second output data includes generating, using the communications unit or the output device, at least one of an output video, an image, or an output speech directed to at least one of:
      diverting the child away from the hazardous event or the hazardous object,
      preventing the hazardous event or the hazardous object from harming the child, or
      communicating information regarding the hazardous event or the hazardous object to the child or a caregiver of the child.

7. The method of claim 1, wherein the at least one person includes at least a child, and the pre-programmed algorithm corresponds to a parental control algorithm for analyzing an action, a speech, or an interaction of the child, the detected object, the detected event, or combinations thereof, the method further comprising:
   analyzing, using the processor, the first detected data and the second detected data based at least on the parental control algorithm and the learned data,
   wherein the second output data corresponds to at least one of:
      a parental notification data for communicating information to a caregiver of the child regarding the action, the speech, or the interaction of the child, the detected object, the detected event, or combinations thereof, or
      a child notification data for communicating information or a warning to the child regarding the action, the speech, or the interaction of the child, the detected object, the detected event, or combinations thereof.

8. The method of claim 1, wherein the item that can be worn or carried is configured to provide vibration feedback to a user.

9. The method of claim 1, wherein the item that can be worn or carried includes or is a computer-based device.

10. A computer-based method of actively and automatically providing personal assistance using an electronic or computer-based device having a processor coupled to at least one sensor, a communications unit, and an output device, the electronic or computer-based device being coupled to or integrated in a robotic device or platform, the method comprising the steps of:
   detecting, using the at least one sensor, a first data associated with at least one person within a proximity of at least one of the at least one sensor;
   detecting, using the at least one sensor, a second data associated with an object, a living being, an event, a place, an environment, or combinations thereof within a proximity of at least one of the at least one sensor;
selectively storing, using the processor, a learned data in a database based on the first detected data, the second detected data, a pre-programmed algorithm stored in the database, or combinations thereof;
passively outputting, using the communications unit or the output device coupled to or in communication with the processor, a first output data upon a request received by the processor or a predetermined or scheduled event stored in the database; and
actively and automatically outputting, using the communications unit or the output device, a second output data based on the first detected data, the second detected data, the learned data, the pre-programmed algorithm, or combinations thereof,
wherein the robotic device or platform is configured to move on a ground surface or in an air space to stay within a proximity of a user to enable or enhance the step of detecting the first detected data and second detected data or to enable or enhance the step of actively and automatically outputting the second output data for enhancing communication with the user, and
wherein the robotic device or platform is a transportation device configured to transport at least the user.

11. The method of claim 10, further comprising actively and automatically outputting, using the processor, a third output data based on the first detected data, the second detected data, the learned data, the pre-programmed algorithm, or combinations thereof,
wherein the output device is an electromechanical device or a controller of the electromechanical device, the electromechanical device being configured to perform a mechanical operation of the robotic platform based on the third output data.

12. The method of claim 10, wherein the step of actively and automatically outputting the second output data further includes at least one of:
actively and automatically generating, using the communications unit or the output device, an output speech, an output image, an output video, or combinations thereof for actively and automatically initiating or participating in the conversation or the interaction with the at least one person, or
actively and automatically generating, using the communications unit or the output device, the output speech, the output image, the output video or combinations thereof for actively communicating a reminder to a user.

13. A computer-based method of actively and automatically providing personal assistance using a robotic device or platform having a processor coupled to at least one sensor, a communications unit, and an output device, the method comprising the steps of:
detecting, using the at least one sensor, a first data associated with at least one person within a proximity of at least one of the at least one sensor;
detecting, using the at least one sensor, a second data associated with an object, a living being, an event, a place, an environment, or combinations thereof within a proximity of at least one of the at least one sensor;
selectively storing, using the processor, a learned data in a database based on the first detected data, the second detected data, a pre-programmed algorithm stored in the database, or combinations thereof;
analyzing, using the processor, a conversation or an interaction based on at least one of the first detected data and the second detected data;
passively outputting, using the communications unit or the output device coupled to or in communication with the processor, a first output data upon a request received by the processor or a predetermined or scheduled event stored in the database; and
actively and automatically outputting, using the communications unit or the output device, a second output data based on the first detected data, the second detected data, the learned data, the preprogrammed algorithm or combinations thereof,
wherein the step of actively and automatically outputting the second output data further includes at least one of:
actively and automatically generating, using the communications unit or the output device, an output speech, an output image, an output video, or combinations thereof for actively and automatically initiating or participating in the conversation or the interaction with the at least one person, or
actively and automatically generating, using the communications unit or the output device, the output speech, the output image, the output video or combinations thereof for actively communicating a reminder to a user.

14. The method of claim 13, further comprising:
changing, using the processor or a controller, a current position of the robotic device or platform or at least one of the at least one sensor to a new position to increase a quantity of or improve a quality of the first detected data or the second detected data, the new position being determined such that the robotic device or platform continuously stays within a proximity of a user as the user moves from a first position to a second position, for enhancing at least one of the conversation or the interaction with the at least one person.

15. The method of claim 13, wherein the step of actively and automatically outputting the second output data is performed using an item that can be worn or carried by a person.

16. A computer-based method of actively and automatically providing personal assistance using a robotic device or platform having a processor coupled to at least one sensor, a communications unit, and an output device, the method comprising the steps of:
detecting, using the at least one sensor, a first data associated with at least one person within a proximity of at least one of the at least one sensor;
detecting, using the at least one sensor, a second data associated with an object, a living being, an event, a place, an environment, or combinations thereof within a proximity of at least one of the at least one sensor;
selectively storing, using the processor, a learned data in a database based on the first detected data, the second detected data, a pre-programmed algorithm stored in the database, or combinations thereof;
passively outputting, using the communications unit or the output device coupled to or in communication with the processor, a first output data upon a request received by the processor or a predetermined or scheduled event stored in the database;
actively automatically outputting, using the communications unit or the output device, a second output data based on the first detected data, the second detected data, the learned data, the pre-programmed algorithm, or combinations thereof; and
actively and automatically improving a quality of or increasing a quantity of the first detected data or the second detected data by performing at least one of:

actively and automatically outputting, using the communications unit or the output device, the second output data in form of a question or an inquiry for eliciting a response or an input from the at least one person, actively and automatically outputting, using the communications unit or the output device, the second output data for participating in a conversation or an interaction with the at least one person, or actively and automatically positioning, using the processor, the at least one sensor in a new position or location that enhances the ability of the at least one sensor to detect the first and second detected data.

17. The method of claim 16, further comprising:
changing, using the processor or a controller, a current position of the robotic device or platform for improving the quality of or increasing the quantity of the first detected data or the second detected data.

18. The method of claim 16, wherein the first detected data corresponds to a visual characteristic, a speech, tactile information, a motion, an interaction, an action, a behavior, a conversation, a characteristic, a location, an identity, an attribute, or combinations thereof associated with the at least one person, and the second detected data corresponds to at least one of:

a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or a characteristic, a type, a location, a temperature, a moisture content, a weather condition, a sound, a visual characteristic, an attribute, or combinations thereof associated with the place or the environment within a proximity of at least one of the at least one sensor.

19. A computer-based method of actively and automatically providing personal assistance using a robotic device or platform having a processor coupled to at least one sensor, a communications unit, and an output device, the method comprising the steps of:

detecting, using the at least one sensor, a first data associated with at least one person within a proximity of at least one of the at least one sensor;

detecting, using the at least one sensor, a second data associated with an object, a living being, an event, a place, an environment, or combinations thereof within a proximity of at least one of the at least one sensor;

selectively storing, using the processor, a learned data in a database based on the first detected data, the second detected data, a pre-programmed algorithm stored in the database, or combinations thereof;

passively outputting, using the communications unit or the output device coupled to or in communication with the processor, a first output data upon a request received by the processor or a predetermined or scheduled event stored in the database; and actively and automatically outputting, using the communications unit or the output device, a second output data based on the first detected data, the second detected data, the learned data, the pre-programmed algorithm, or combinations thereof, wherein the at least one sensor is at least one of an image sensor, a vibration sensor, a microphone, a proximity detector, a position detector, a force sensor, a distance sensor, a laser scanner, or a radar sensor, and the at least one sensor is integrated in or coupled to the robotic device or platform.

20. The method claim 19, wherein the at least one person includes at least a child, and the pre-programmed algorithm includes a hazard detection algorithm, the method further comprising:

determining, using the processor, a hazardous event or a hazardous object within a proximity of the child having a possibility of inflicting emotional or physical harm to the child, based on the hazard detection and analysis algorithm, the first detected data, and the second detected data, wherein the step of actively and automatically outputting the second output data includes generating, using the communications unit or the output device, at least one of an output video, an image, or an output speech directed to at least one of:

diverting the child away from the hazardous event or the hazardous object, preventing the hazardous event or the hazardous object from harming the child, or communicating information regarding the hazardous event or the hazardous object to the child or a caregiver of the child.

21. The method of claim 19, wherein the first detected data corresponds to a visual characteristic, a speech, tactile information, a motion, an interaction, an action, a behavior, a conversation, a characteristic, a location, an identity, an attribute, or combinations thereof associated with the at least one person, and the second detected data corresponds to at least one of:

a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or a characteristic, a type, a location, a temperature, a moisture content, a weather condition, a sound, a visual characteristic, an attribute, or combinations thereof associated with the place or the environment within a proximity of at least one of the at least one sensor.

22. A computer-based method of actively and automatically providing personal assistance using a robotic device or platform having a processor coupled to at least one sensor, a communications unit, and an output device, the method comprising the steps of:

detecting, using the at least one sensor, a first data associated with at least one person within a proximity of at least one of the at least one sensor;

detecting, using the at least one sensor, a second data associated with an object, a living being, an event, a place, an environment, or combinations thereof within a proximity of at least one of the at least one sensor;

selectively storing, using the processor and in a database that includes or is in communication with a cloud-based database, a learned data based on the first detected data, the second detected data, a pre-programmed algorithm stored in the cloud-based database, or combinations thereof;

passively outputting, using the communications unit or the output device coupled to or in communication with the processor, a first output data upon a request received by the processor or a predetermined or scheduled event stored in the cloud-based database; and actively and automatically outputting, using the communications unit or the output device, a second output data based on the first detected data, the second detected data, the learned data, the pre-programmed algorithm, or combinations thereof, wherein the step of actively and automatically outputting, using the communications unit or the output device, the second output data includes at least one of:

displaying, using a screen or a visual projection system coupled to or in communication with the communications unit or the output device, an output image or an output video, or generating, using a speaker coupled to or in communication with the communications unit or the output device, an output speech.

23. The method of claim 22, further comprising:
analyzing, using the processor, a conversation or an interaction based on at least one of the first detected data and the second detected data,
wherein content of at least one of the output image, the output video, or the output speech is based on the analyzed conversation or interaction.

24. The method of claim 22, wherein the step of actively and automatically outputting the second output data is performed using an item that can be worn or carried by a person.

25. A computer-based method of actively and automatically providing personal assistance using a robotic device or platform having a processor coupled to at least one sensor, a communications unit, and an output device, the method comprising the steps of:

detecting, using the at least one sensor, a first data associated with at least one person within a proximity of at least one of the at least one sensor;

detecting, using the at least one sensor, a second data associated with an object, a living being, an event, a place, an environment, or combinations thereof within a proximity of at least one of the at least one sensor;

selectively storing, using the processor and in a database that includes or is in communication with a cloud-based database, a learned data based on the first detected data, the second detected data, a pre-programmed algorithm stored in the cloud-based database, or combinations thereof;

passively outputting, using the communications unit or the output device coupled to or in communication with the processor, a first output data upon a request received by the processor or a predetermined or scheduled event stored in the cloud-based database;

actively and automatically outputting, using the communications unit or the output device, a second output data based on the first detected data, the second detected data, the learned data, the pre-programmed algorithm, or combinations thereof;

transmitting, using the processor and the cloud-based database, the first detected data, the second detected, the first output data, the second output data, or combinations thereof to an external device coupled to or in communication with the cloud-based database; and receiving, using the processor and the cloud-based database, an input data from the external device.

26. The method of claim 25, wherein the external device is a computer-based portable electronic device.

27. The method of claim 25, wherein the robotic device or platform is configured to move on a ground surface or in an air space to stay within a proximity of a user to enable or enhance the step of detecting the first detected data and second detected data or to enable or enhance the step of actively and automatically outputting the second output data for enhancing communication with the user.

28. A computer-based method of actively and automatically providing personal assistance using a robotic device or platform having a processor coupled to at least one sensor, a communications unit, and an output device, the method comprising the steps of:

detecting, using the at least one sensor a first data associated with at least one person within a proximity of at least one of the at least one sensor wherein the at least one person includes a user with disabilities or suffering from health or memory complications;

detecting, using the at least one sensor, a second data associated with an object, a living being, an event, a place, an environment, or combinations thereof within a proximity of at least one of the at least one sensor;

selectively storing, using the processor, a learned data in a database based on the first detected data, the second detected data, a pre-programmed algorithm stored in the database, or combinations thereof;

passively outputting, using the communications unit or the output device coupled to or in communication with the processor, a first output data upon a request received by the processor or a predetermined or scheduled event stored in the database; and actively and automatically outputting, using the communications unit or the output device, a second output data based on the first detected data, the second detected data, the learned data, the pre-programmed algorithm, or combinations thereof, wherein the step of actively and automatically outputting the second output data further includes at least one of:

analyzing, using the processor, the first detected data and the second detected data, or associating the first detected data and the second detected data with the learned data corresponding to the detected person, object, living being, event, place, environment, or combinations thereof, and wherein the second output data corresponds to a reminder data directed to communicating information to the user with respect to identification, characteristics, location, actions, and interactions of the at least one person, the object, the living being, the event, the place, the environment, or combinations thereof.

29. The method of claim 28, wherein:
the first detected data corresponds to a visual characteristic, a speech, tactile information, a motion, an interaction, an action, a behavior, a conversation, a characteristic, a location, an identity, an attribute, or combinations thereof associated with the at least one person,
the second detected data corresponds to at least one of:
a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or
a characteristic, a type, a location, a temperature, a moisture content, a weather condition, a sound, a visual characteristic, an attribute, or combinations thereof associated with the place or the environment within a proximity of at least one of the at least one sensor.

30. The method of claim 28, further comprising:
analyzing, using the processor, the first detected data and the second detected data based on the learned data corresponding to the detected at least one person, object, living being, event, place, environment, or combinations thereof, wherein the steps of selectively storing the database and actively and automatically outputting the second output data are further based on the analyzed first and second detected data.

31. A computer-based method of actively and automatically providing personal assistance using a robotic device or platform having a processor coupled to at least one sensor, a communications unit, and an output device, the method comprising the steps of:
   detecting, using the at least one sensor, a first data associated with at least one person within a proximity of at least one of the at least one sensor;
   detecting, using the at least one sensor, a second data associated with an object, a living being, an event, a place, an environment, or combinations thereof within a proximity of at least one of the at least one sensor;
   selectively storing, using the processor, a learned data in a database based on the first detected data, the second detected data, a pre-programmed algorithm stored in the database, or combinations thereof;
   analyzing, using the processor, health, exercise, or diet activities of the at least one person based on the detected data;
   passively outputting, using the communications unit or the output device coupled to or in communication with the processor, a first output data upon a request received by the processor or a predetermined or scheduled event stored in the database; and
   actively and automatically outputting, using the communications unit or the output device, a second output data based on the first detected data, the second detected data, the learned data, the pre-programmed algorithm, or combinations thereof, wherein the step of actively and automatically outputting, using the communications unit or the output device, the second output data includes at least one of:
      outputting, using the communications unit or the output device, the second output data to a health professional for assisting the health professional in evaluation of the health, exercise, or diet activities of the at least one person, or
      outputting, using the communications unit or the output device, the second output data to the at least one person for outputting a recommendation associated with the health, exercise, or diet activities.

32. The method of claim 31, wherein:
   the first detected data corresponds to a visual characteristic, a speech, tactile information, a motion, an interaction, an action, a behavior, a conversation, a characteristic, a location, an identity, an attribute, or combinations thereof associated with the at least one person,
   the second detected data corresponds to at least one of:
      a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or
      a characteristic, a type, a location, a temperature, a moisture content, a weather condition, a sound, a visual characteristic, an attribute, or combinations thereof associated with the place or the environment within a proximity of at least one of the at least one sensor.

33. The method of claim 31, further comprising:
   analyzing, using the processor, the first detected data and the second detected data based on the learned data corresponding to the detected at least one person, object, living being, event, place, environment, or combinations thereof,
   wherein the steps of selectively storing the database and actively and automatically outputting the second output data are further based on the analyzed first and second detected data.

34. A computer-based method of actively and automatically providing personal assistance using a robotic device or platform having a processor coupled to at least one sensor a communications unit and an out ut device the method comprising the steps of:
   detecting, using the at least one sensor, a first data associated with at least one person within a proximity of at least one of the at least one sensor;
   detecting, using the at least one sensor, a second data associated with an object, a living being, an event, a place, an environment, or combinations thereof within a proximity of at least one of the at least one sensor;
   selectively storing, using the processor, a learned data in a database based on the first detected data, the second detected data, a pre-programmed algorithm stored in the database, or combinations thereof, wherein the pre-programmed algorithm corresponds to appropriateness algorithm rules for determining information content of the second output data, privacy concerns of a user, context of the detected event, or combinations thereof;
   passively outputting, using the communications unit or the output device coupled to or in communication with the processor, a first output data upon a request received by the processor or predetermined or scheduled event stored in the database;
   analyzing, using the processor, the detected first data or the detected second data based on the appropriateness algorithm rules and the learned data; and
   actively and automatically outputting, using the communications unit or the output device, a second output data based on the analyzed first data or the analyzed second data.

35. The method of claim 34, wherein the at least one person includes a user with disabilities or suffering from health or memory complications, and the pre-programmed algorithm is defined based on the disabilities or the health or memory complications.

36. The method of claim 34, further comprising actively and automatically outputting, using the processor, a third output data based on the first detected data, the second detected data, the learned data, the pre-programmed algorithm, or combinations thereof,
   wherein the output device is an electromechanical device or a controller of the electromechanical device, the electromechanical device being configured to perform a mechanical operation to assist a user based on the third output data.

37. A computer-based method of actively and automatically providing personal assistance using a robotic device or platform, the method comprising the steps of:
   detecting, using at least one sensor, a first detected data associated with a person or a user within a proximity of at least one of the at least one sensor;
   detecting, using the at least one sensor, a second detected data associated with an object, a living being, an event, a place, an environment, or combinations thereof within a proximity of at least one of the at least one sensor;
   changing, using a processor or a controller, a current position of the robotic device or platform or at least one of the at least one sensor to a new position to increase a quantity of or improve a quality of the first detected data or the second detected data, the new position being determined such that the robotic device or platform continuously stays within a proximity of a user as the user moves from a first position to a second position;

analyzing, using the processor, the first detected data and the second detected data based on the learned data corresponding to the person, the object, the living being, the event, the place, the environment, or combinations thereof;

selectively storing, using the processor, the learned data in a database based on the first detected data, the second detected data, a pre-programmed algorithm stored in the database, or combinations thereof;

passively outputting, using a communications unit coupled to or in communication with the processor, a first output data upon a request received by the processor or a predetermined or scheduled event stored in the database; and actively and automatically outputting, using the communications unit, a second output data based on the analyzed first detected data, the analyzed second detected data, the learned data, the pre-programmed algorithm, or combinations thereof.

38. The method of claim 37, further comprising actively and automatically outputting, using the processor, a third output data based on the first detected data, the second detected data, the learned data, the pre-programmed algorithm, or combinations thereof, wherein the output device is an electromechanical device or a controller of the electromechanical device, the electromechanical device being configured to perform a mechanical operation of the robotic platform based on the third output data.

39. The method of claim 37, wherein:

the first detected data corresponds to a visual characteristic, a speech, tactile information, a motion, an interaction, an action, a behavior, a conversation, a characteristic, a location, an identity, an attribute, or combinations thereof associated with the at least one person, the second detected data corresponds to at least one of:

a motion, a sound, an interaction, an action, a tactile information, a visual characteristic, a location, an identity, an attribute, or combinations thereof associated with the detected object, living being, event, place, environment, or combinations thereof within a proximity of at least one of the at least one sensor, or a characteristic, a type, a location, a temperature, a moisture content, a weather condition, a sound, a visual characteristic, an attribute, or combinations thereof associated with the place or the environment within a proximity of at least one of the at least one sensor.

* * * * *